US011559502B2

(12) United States Patent
Janssen et al.

(10) Patent No.: US 11,559,502 B2
(45) Date of Patent: Jan. 24, 2023

(54) TREATMENT OF MENSTRUAL CYCLE-INDUCED SYMPTOMS

(71) Applicant: Period Pill BV, Amsterdam (NL)

(72) Inventors: Merel Janssen, Baambrugge (NL); Jochem Stijn Edgar, Baambrugge (NL); Ezekiel Golan, Vancouver (CA)

(73) Assignee: Period Pill BV, Amsterdam (NL)

( * ) Notice: Subject to any disclaimer, the term of this patent is extended or adjusted under 35 U.S.C. 154(b) by 0 days.

(21) Appl. No.: 17/637,859

(22) PCT Filed: Aug. 26, 2020

(86) PCT No.: PCT/IB2020/057967
§ 371 (c)(1),
(2) Date: Feb. 24, 2022

(87) PCT Pub. No.: WO2021/038460
PCT Pub. Date: Mar. 4, 2021

(65) Prior Publication Data
US 2022/0265581 A1 Aug. 25, 2022

Related U.S. Application Data

(60) Provisional application No. 62/891,438, filed on Aug. 26, 2019.

(51) Int. Cl.
A61K 31/137 (2006.01)
A61P 15/00 (2006.01)
(52) U.S. Cl.
CPC ............ A61K 31/137 (2013.01); A61P 15/00 (2018.01)

(58) Field of Classification Search
CPC .............................. A61K 31/137; A61P 15/00
See application file for complete search history.

(56) References Cited

U.S. PATENT DOCUMENTS

| 2004/0048919 | A1 | 3/2004 | Dreon et al. |
| 2004/0127409 | A1 | 7/2004 | McMichael et al. |
| 2006/0241172 | A1 | 10/2006 | Zhou et al. |
| 2006/0241176 | A1 | 10/2006 | Stack et al. |
| 2007/0098819 | A1 | 5/2007 | Thys-Jacob |

(Continued)

FOREIGN PATENT DOCUMENTS

| WO | WO 2005/049088 | 6/2005 |
| WO | WO 2013/171146 | 11/2013 |
| WO | WO 2019/026019 | 2/2019 |
| WO | WO 2021/038460 | 3/2021 |

OTHER PUBLICATIONS

Brockington, Curr Psychiatry Rep (2011) 13:193-197 (Year: 2011).*
International Preliminary Report on Patentability dated Mar. 10, 2022 from the International Bureau of WIPO Re. Application No. PCT/IB2020/057967. (7 Pages).

(Continued)

Primary Examiner — San Ming R Hui

(57) ABSTRACT

The present invention relates to methods of treatment of menstrual cycle induced disorders and symptoms with cathinone, particularly methods employing 3-methyl methcathinone (3-MMC). The present invention also relates to kits comprising 3-MMC for use in the treatment of subjects suffering from menstrual cycle induced disorders and symptoms. In particular, methods and kits for therapy of menstrual cycle induced disorders and symptoms with 3-MMC for a variety of disorders and/or conditions, including PMS, PMDD and perimenstrual disorders are provided.

23 Claims, 3 Drawing Sheets

(56) References Cited

U.S. PATENT DOCUMENTS

| | | |
|---|---|---|
| 2007/0203078 A1 | 8/2007 | Mody et al. |
| 2007/0255278 A1 | 11/2007 | Nobis et al. |
| 2008/0160083 A1 | 7/2008 | Morrow |
| 2008/0262071 A1 | 10/2008 | Dinan et al. |
| 2010/0172916 A1 | 7/2010 | Gant et al. |
| 2011/0207718 A1 | 8/2011 | Bird |
| 2013/0171269 A1 | 7/2013 | Rutenberg et al. |
| 2014/0356424 A1 | 12/2014 | Vilar et al. |
| 2016/0000815 A1 | 1/2016 | Bird |
| 2016/0058428 A1 | 3/2016 | Shinar et al. |
| 2016/0367614 A1 | 12/2016 | Kim et al. |
| 2019/0099399 A1 | 4/2019 | Ueno et al. |

OTHER PUBLICATIONS

International Seach Report and the Written Opinion dated Nov. 18, 2020 from the International Searching Authority Re. Application No. PCT/IB2020/057967. (10 Pages).

Amoroso et al. "Treating Posttraumalic Stress Disorder With MDMA-Assisted Psychotherapy: A Preliminary Meta-Analysis and Comparison to Prolonged Exposure Therapy", The Journal of Psychopharmacology, 30(7): 595-600, Published Online Apr. 26, 2016.

Danforth et al. "MDMA-Assisted Therapy: A New Treatment Model for Social Anxiety in Autistic Adults", Progress in Neuro-Psychopharmacology & Biological Psychiatry, 64: 237-249, Available Online Mar. 25, 2015.

Schoep et al. "The Impact of Menstrual Symptoms on Everyday Life: A Survev Among 42,879 Women", American Journal of Obstetrics & Gynecology, 220(6): 569.1-569.7, Published Online Mar. 15, 2019.

* cited by examiner

Figure 1: Most Commonly Reported Menstrual Cycle-Induced Complaints among Subjects
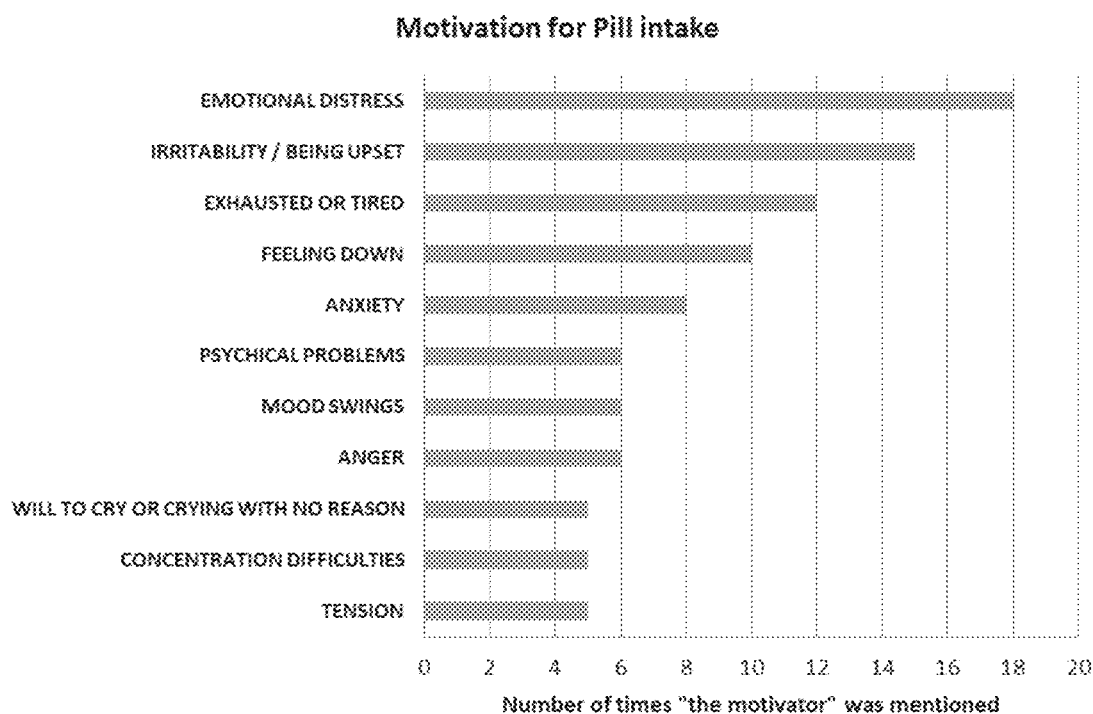

Figure 2: Most Commonly Reported Benefits of 3-MMC for Menstrual Cycle-Induced Symptoms among Subjects
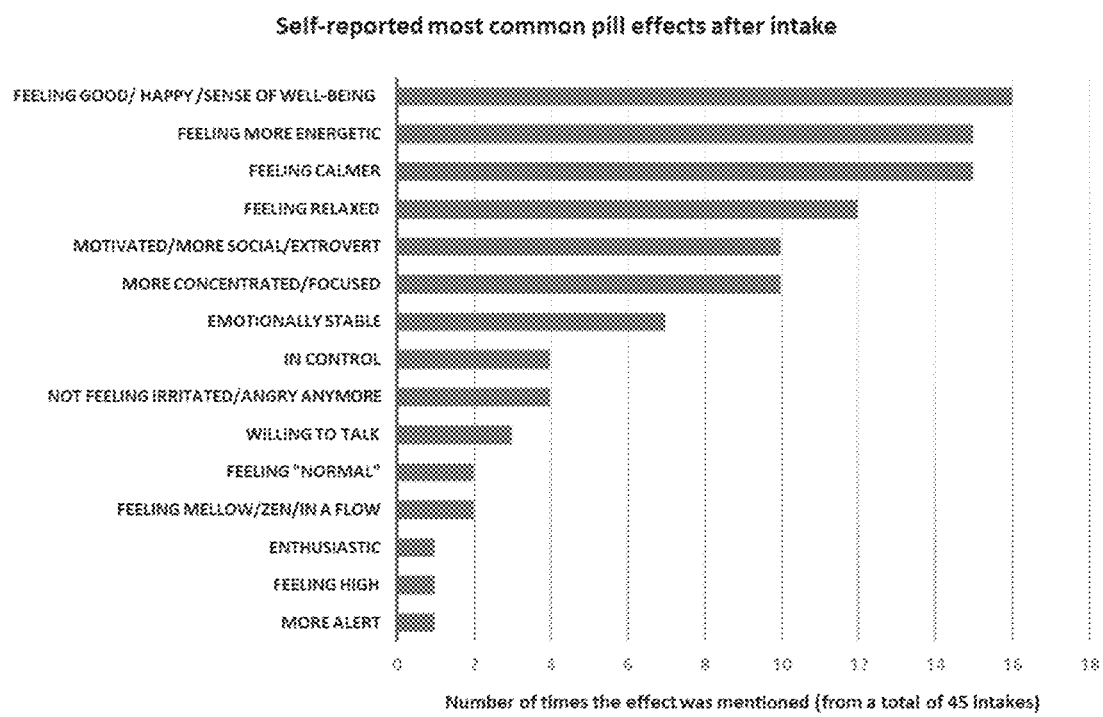

Figure 3: Most Common Reported Side Effects of 3-MMC for Menstrual Cycle-Induced Symptoms in Subjects
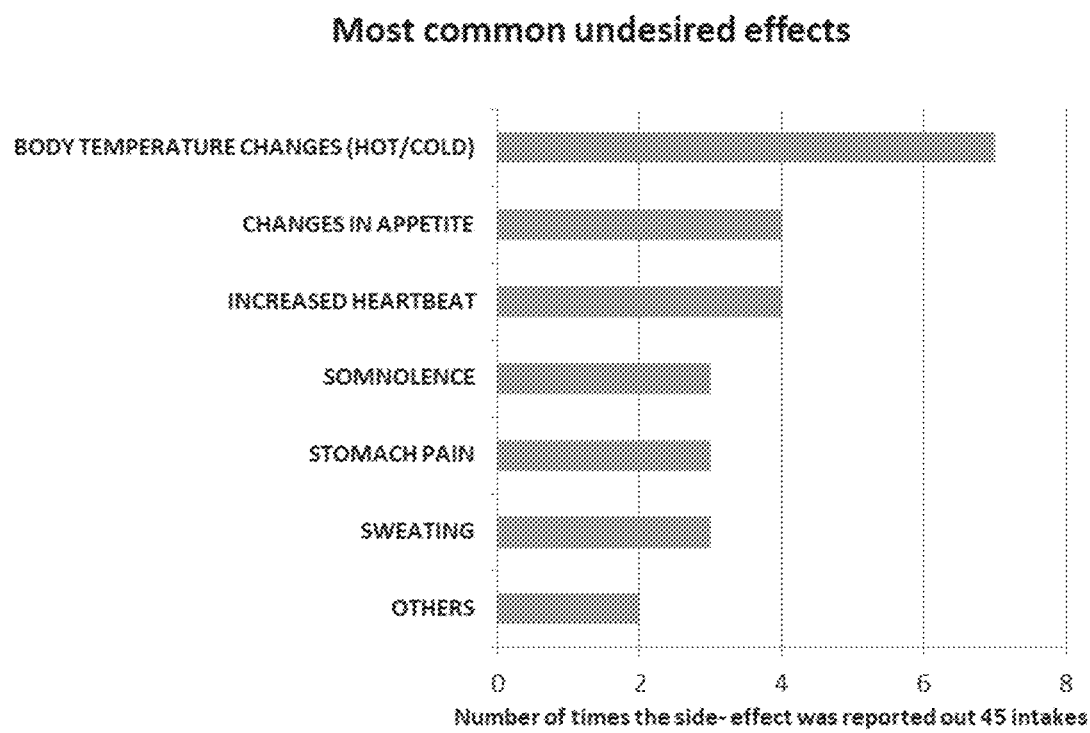

TREATMENT OF MENSTRUAL CYCLE-INDUCED SYMPTOMS

RELATED APPLICATIONS

This application is a National Phase of PCT Patent Application No. PCT/IB2020/057967 having International filing date of Aug. 26, 2020, which claims the benefit of priority under under 35 USC § 119(e) of U.S. Provisional Patent Application No. 62/891,438 filed on Aug. 26, 2019.

The contents of the above applications are all incorporated by reference as if fully set forth herein in their entirety.

FIELD AND BACKGROUND OF THE INVENTION

Menstrual symptoms, including heavy menstrual bleeding, dysmenorrhea, and significant perimenstrual mood disorders (Premenstrual Syndrome-PMS, Premenstrual Dysphoria Disorder-PMDD), are common gynecologic conditions. In addition to the common somatic symptoms, common menstrual cycle-induced behavioral/mood changes include depression, angry outbursts, irritability, crying spells/jags, anxiety, confusion, social withdrawal, reduced concentration, insomnia, fatigue, changes in libido (Amer Coll. Obstet. And Gynaecol FAQ-PMS, 2015). When asked, between 22.5% and 35% of women considered their menstrual bleeding heavy, and 34-94% experience pain during their menstrual period. Menstrual symptoms have a significant impact on quality of life. Furthermore, they account for substantial healthcare use. Annual costs for patients with heavy menstrual bleeding are estimated to exceed $2000 per patient, mainly owing to work absence and lost productivity. Depending on the national regulations on sick leave, the costs of absenteeism may vary between countries. In younger women, menstrual symptoms may result in absence from school or lower levels of performance. Absences of adolescent girls who do not attend school because of dysmenorrhea range from 7.7% to 57.8%, whereas 21.5% report missing out on social activities.

Despite the large influence on women's lives, collectively and individually, several studies have shown that most women with dysmenorrhea do not seek help, highlighting the public health impact of menstrual problems, including reduced quality of life and high medical and societal costs. Although little is known about the prevalence of menstrual symptoms in the general nonselected population, a recent study (Schoep et al, 2019 Am J Obs Gyn 220:569) reported a high prevalence of dysmenorrhea (85%), behavioral and mood complaints (77%) and significant somatic complaints (50%) among more than 40,000 women interviewed. Nearly 40% of the respondents reported overall impaired activity during their menses.

Typical treatment options for symptoms of perimenstrual conditions are wide-ranging, including diet, life-style changes for mild-moderate symptoms to medical and non-conventional solutions for more severe forms. The American College of Obstetricians and Gynecologists recommends exercise and dietary changes (e.g. complex carbohydrates and calcium rich foods), calcium supplementation and improved sleep for mild to moderate perimenstrual symptoms. Pharmacological solutions for severe symptoms (hormonal contraceptives, diuretics, NSAIDS) mostly address somatic aspects, while anti-depressants, dopamine agonists, anxiolytics, and other psychoactive drugs are prescribed for behavioral/mood symptoms. However, the pharmacologically active agents currently used to treat menstrual cycle-induced symptoms are less than ideal, being costly and having significant side effects. Drugs such as serotonin re-uptake inhibitors (e.g., fluoxetine and sertraline (both FDA approved for PMDD), anti-inflammatory agents, anxiolytics, hormones, dopamine agonists, and diuretics are sometimes suggested for treatment of PMS, but cost, efficacy and side effects of these treatments are significant concerns. (Most antidepressants have rather serious side effects such as heartbeat, hallucinations, loss of coordination, severe dizziness, severe nausea/vomiting/diarrhea, twitching muscles, and more).

Other proposed remedies for menstrual cycle-induced symptoms include, inter alia, alpha-tocopherol-omega-3 polyunsaturated fatty acid combinations, nerve growth factor, 2C 5-HT receptor agonists, calcium and vitamin D supplementation, GABA-A receptor agonists, pyridoxine, pindolol, magnesium, oxytocin-releasing agents, phosphatidyl-L serine and magnesium combinations (see US Patent Application Publications 2014/0356424; 2016/0058428; 2013/0171269; 2008/0262071; 2008/0160083; 2007/0255278; 2007/0203078; 2007/0098819; 2006/0241172; 2006/0241176; 2004/0127409; 2004/0048919; 2019/0099399; 2016/0367614).

Psychostimulants and 3-MMC:

Certain psycho-active drugs have been suggested for alleviation of behavioral and mood-related menstrual cycle-induced symptoms and disorders. Traditional psychostimulants such as amphetamine, cocaine or methylenedioxymethamphetamine (MDMA) all primarily target monoaminergic systems, leading to increased extracellular levels of serotonin (5-HT), dopamine (DA), and/or noradrenaline (NA). Experience with MDMA and cycloserine, as well as other psychoactive compounds has suggested benefit for mood and behavioral disorders, but has also revealed their shortcomings for therapeutic use. In general, amphetamines are associated with risk of amphetamine-psychosis, depression and cognitive impairment. In particular, serotonergic drugs such as MDMA, by stimulating an excess release of serotonin (and therefore possibly also triggering down-regulation of serotonin receptors in the brain), can create a rebound serotonin depletion and decreased sensitivity to the neurotransmitter following it's use, experienced by the user as depression and often lasting several days or more (for a review, see Danforth et al, Prog Neuro-Psych and Biol Psych, 2016, 64:237-249, or Amoroso et al, J. Psychopharm 2016, 30:595-600).

The present invention relates to the use of 3-methyl methcathinone (3-MMC) for menstrual cycle induced symptoms. The cathinones are substituted amphetamines, differing in the character and location of the side residues around the central ring. All of 2-, 3- and 4-Methyl-methcathinone (2-, 3- and 4-MMC) are psychoactive drugs, producing increased alertness, wakefulness, euphoria and appetite suppression. Therapeutic use of 4-MMC as a psychostimulant has been proposed in US Patent Publications 2011/0207718; 2010/0172916, 2016/0000815. Therapeutic use of 3-MMC has been proposed in PCT Publication 2019/026019.

SUMMARY OF THE INVENTION

According to an aspect of some embodiments of the present invention, there is provided a method of treating at least one menstrual-cycle-induced symptom in a subject in need thereof, the method comprising: determining a time at which the at least one menstrual-cycle-induced symptom is expected to occur, or has occurred; and administering a therapeutically effective amount of 3-methylmethcathinone (3-MMC), so as to treat the menstrual-cycle-induced symptom.

According to some embodiments of the invention, the at least one menstrual-cycle-induced symptom is expected to occur, or has occurred between 1-15 days prior to onset of menses.

According to some embodiments of the invention the at least one menstrual-cycle-induced symptom is expected to occur, or has occurred between 1-7 days prior to onset of menses.

According to some embodiments of the invention the at least one menstrual-cycle-induced symptom is expected to occur, or has occurred between 1-10 days following onset of menses.

According to some embodiments of the invention the at least one menstrual-cycle-induced symptom is expected to occur, or has occurred between 1-7 days following onset of menses.

According to some embodiments of the invention, the at least one menstrual-cycle-induced symptom is expected to occur, or has occurred between 1-7 days prior to and between 1-7 days following onset of menses.

According to some embodiments of the invention, the administering occurs prior to the time at which the menstrual-cycle-induced symptom is expected to occur.

According to some embodiments of the invention, the administering occurs 1-5 days prior to the time at which the menstrual-cycle-induced symptom is expected to occur.

According to some embodiments of the invention, the administering occurs 1-3 days prior to the time at which the menstrual-cycle-induced symptom is expected to occur.

According to some embodiments of the invention, the administering occurs during the time at which the menstrual-cycle-induced symptom is expected to occur, or has occurred.

According to some embodiments of the invention, the administering is discontinued at the time at which the menstrual-cycle-induced symptom is relieved.

According to some embodiments of the invention, the administering is discontinued 1-7 days from onset of menses.

According to some embodiments of the invention, the administering is discontinued 2-5 days from onset of menses.

According to some embodiments of the invention, the administering is discontinued 1-7 days from conclusion of menstruation.

According to some embodiments of the invention, the administering is discontinued 2-5 days from conclusion of menstruation.

According to some embodiments of the invention, the at least one menstrual-cycle-induced symptom is a symptom of a menstrual-cycle induced condition selected from the group consisting of perimenstrual disorder, Premenstrual Syndrome (PMS) and Premenstrual Dysphoric Disorder (PMDD).

According to some embodiments of the invention, the at least one menstrual-cycle-induced symptom is a somatic symptom.

According to some embodiments of the invention, the at least one menstrual-cycle-induced symptom is a mood and/or behavioral symptom.

According to some embodiments of the invention, the at least one menstrual-cycle-induced symptom is selected from the group consisting of lethargy, eating disorders, forgetfulness, sleep disturbances, appetite changes, poor concentration, decreased interest, social withdrawal, irritability, mood swings, anxiety, tension, depression and feelings of lack of control.

According to some embodiments of the invention, the at least one menstrual-cycle-induced symptom comprises at least two or more symptoms.

According to some embodiments of the invention, the 3-MMC is administered in an amount in the range of 5 to 100 mg per administration.

According to some embodiments of the invention, the 3-MMC is administered in an amount in the range of 10-65 mg per administration.

According to some embodiments of the invention, the 3-MMC is administered in an amount of 12.5, 25, 35, 40 or 50 mg per administration.

According to some embodiments of the invention, the 3-MMC is administered in an amount of 25 mg per administration.

According to another aspect of some embodiments of the present invention, there is provided a kit for use in treating at least one menstrual-induced symptom in a subject comprising at least one unit dosage comprising a therapeutically effective amount of 3-methylmethcathinone (3-MMC) and instructions for the administration of the 3-MMC before, during or following the time at which the menstrual-cycle-induced symptom is expected to occur, or has occurred, and packaging material.

According to some embodiments of the invention, the kit further comprises a device for determining the time at which the at least one menstrual-cycle-induced symptom is expected to occur, or has occurred in the subject.

According to some embodiments of the invention, the kit is accompanied by a digital computer interface for recording chronology and character of the at least one menstrual-cycle-induced symptom.

According to some embodiments of the invention, the interface is of a cellular phone application, the kit further comprises a barcode for downloading or activating the application. According to some embodiments of the invention, the unit dosage comprises between 5 and 100 mg 3-MMC.

According to some embodiments of the invention, the unit dosage comprises between 10 and 60 mg 3-MMC.

According to some embodiments of the invention, the unit dosage comprises 12.5 mg 3-MMC.

According to some embodiments of the invention, the unit dosage comprises 25 mg 3-MMC.

According to some embodiments of the invention, the unit dosage comprises 50 mg 3-MMC.

According to some embodiments of the invention, the kit comprises at least one unit dosage of 12.5 mg 3-MMC and at least one unit dosage of 25 mg 3-MMC.

According to some embodiments of the invention, the kit comprises at least one unit dosage of 25 mg 3-MMC and at least one unit dosage of 50 mg 3-MMC.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a histogram showing the common menstrual cycle-induced symptoms most often cited as motivation for use of 3-MMC among study subjects;

FIG. 2 is a histogram showing the most commonly reported benefits of 3-MMC among the study subjects;

FIG. 3 is a histogram showing the most commonly reported undesired effects of 3-MMC among the study subjects.

DESCRIPTION OF SPECIFIC EMBODIMENTS OF THE INVENTION

The present invention relates to methods of treating menstrual cycle-induced symptoms and disorders with 3-methyl methcathinone (3-MMC). The present invention also relates to kits comprising 3-MMC for use in the treatment of menstrual cycle-induced symptoms and disorders.

The signs and symptoms of menstrual cycle-induced disorders are physical and psychological or behavioral, presenting a temporal relationship with the menstrual cycle and with features repeating in each new cycle. Physical symptoms that are typically associated with PMS include dysmenorrhea, acne, bloating, breast tenderness, dizziness, fatigue, headache, hot flashes, nausea, diarrhea, constipation, heart palpitations, swelling of the hands and feet, and cramps. Affective and cognitive symptoms include mood swings, angry outbursts, violent tendencies, anxiety, nervousness, tension, difficulty concentrating, depression, crying easily, depression, food cravings, forgetfulness, irritability, increased appetite, mood swings, and increased emotional sensitivity.

PMDD is a more severe form of PMS. The behavioral and mood-related symptoms of PMS and PMDD can be just as debilitating as the physical symptoms, resulting in lost work time, expense and disruption of family and social life.

Some methyl methcathinones, in particular 2- and 4-MMC, are potent psychostimulants, but are considered unsuitable for use in alleviating menstrual cycle-induced symptoms due to the pronounced anxiety, stress and other undesirable features of their psychoactive effects.

Surprisingly, the present inventors have shown that, when provided in anticipation of, at onset of or even following the onset of menstrual cycle-induced symptoms (e.g. PMS, PMDD), even a relatively low dose and limited regimen of 3-MMC administration was effective in relieving most frequently cited symptoms and even provided a lasting improvement in quality of life for sufferers of behavioral and mood-related menstrual cycle-induced symptoms, particularly for women previously refractory to conventional remedies with minimal risk of untoward side effects. Inter alia, the inventors have shown that 3-MMC can be effective in reducing the severity of some of the somatic menstrual cycle-induced symptoms.

Before explaining at least one embodiment of the invention in detail, it is to be understood that the invention is not necessarily limited in its application to the details set forth in the following description. The invention is capable of other embodiments or of being practiced or carried out in various ways.

As noted, work or school absence accounts for a significant portion of the personal and social/economic cost of menstrual cycle-induced symptoms, for sufferers, their families and the society at large. Indeed, the present inventors found that emotional distress, irritability, being upset and fatigue or exhaustion were most frequent indications for taking 3-MMC for menstrual cycle-induced symptoms among the women in the sample population. For these women, 3-MMC reportedly enhanced their overall sense of well-being, increased energy levels, induced calmness and relaxation and heightened abilities of concentration.

Surprisingly, the inventors observed that 3-MMC can have a cumulative positive effect on the women: after 2 or more administrations over a relatively brief period (about 24 hours), the positive effects of 3-MMC reportedly persisted, with apparent enhancement of the effects of the subsequent administrations.

Thus, according to some embodiments, the present invention provides a method of treating at least one menstrual cycle-induced symptom in a subject in need thereof, the method comprising determining a time at which the at least one menstrual cycle-induced symptom is expected to occur, or has occurred, and administrating a therapeutically effective amount of 3-methylmethcathinone (3-MMC), so as to treat the menstrual cycle-induced symptom.

As used herein, the term "treating" refers to inhibiting, preventing or arresting the development of a symptom and/or causing the reduction, remission, or regression of that symptom. Those of skill in the art will understand that various methodologies and assays can be used to assess the development of a symptom, and similarly, various methodologies and assays may be used to assess the reduction, remission or regression of the symptom. As used herein, the terms "amelioration", "relief" or "alleviation" of symptoms refers to improvement of the state of the symptoms of a subject; the amelioration, relief or alleviation of a symptom (e.g. fatigue, emotional distress) is the counter-acting of the negative aspects of the symptom. Amelioration, relief or alleviation includes, but does not require complete recovery or complete prevention of a menstrual cycle-induced symptom. In the context of the present invention, amelioration, relief or alleviation is at least about 10%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95% reduction in the reported or measured levels of menstrual cycle-induced symptoms.

As used herein, the phrase "menstrual cycle-induced symptom" refers to a symptom experienced by a woman which occurs cyclically (repeats) in association with the certain portions of the menstrual cycle. In particular embodiments, the symptom occurs in association with certain portions of the menstrual cycle, and remits with transition into another portion of the cycle. In some embodiments, menstrual cycle-induced symptoms include, but are not limited to symptoms of perimenstrual behavioral and mood disorders, such as Premenstrual Syndrome (PMS) and Premenstrual Dysphoria Disorder (PMDD), and perimenstrual somatic symptoms, such as dysmenorrhea and bloating.

As used herein, PMS refers to "the cyclic recurrence of distressing physical, emotional, and behavioral symptoms that affect a woman's health, relationships, and/or occupational functioning". Premenstrual dysphoric disorder (PMDD) is a severe disabling extension of PMS. PMS and PMDD symptom patterns can vary from a low severity of symptoms or the escalation of symptom frequency and severity during premenstrual phase of the cycle to a sudden absence of symptoms after onset of menses. The severity, number, and duration of symptoms affect the intensity of PMS and PMDD.

Both PMS and PMDD involve mood and behavioral symptoms. In some embodiments, menstrual cycle-induced mood and/or behavioral symptoms include, but are not limited to lethargy, eating disorders, forgetfulness, sleep disturbances, appetite changes, poor concentration, decreased interest, social withdrawal, irritability, mood swings, anxiety, tension, depression and a sense of lack of control.

Both PMS and PMDD can include cyclic recurrence of mood swings, irritability or anger, depressed mood anxiety and tension, decreased interest in usual activities, difficulty in concentration, lethargy, appetite changes, disruption of sleep patterns and feeling overwhelmed.

In some embodiments, the menstrual cycle-induced symptom is a symptom of PMDD. In some embodiments, PMDD is diagnosed by the presence of at least 5 of the following 11 symptoms (including at least 1 of the first 4 listed) in the final week before the onset of menses, start to improve within a few days after the onset of menses, and become minimal or absent in the week postmenses:

Symptoms:
1. Marked lability (e.g., mood swings)
2. Marked irritability or anger
3. Markedly depressed mood
4. Marked anxiety and tension
5. Decreased interest in usual activities
6. Difficulty in concentration
7. Lethargy and marked lack of energy
8. Marked change in appetite (e.g., overeating or specific food cravings)
9. Hypersomnia or insomnia
10. Feeling overwhelmed or out of control
11. Physical symptoms (e.g., breast tenderness or swelling, joint or muscle pain, a sensation of 'bloating' and weight gain)

In some embodiments, PMDD is defined according to the criteria of the Diagnostic and Statistical Manual (DSM-V). According to the DSM-V, additional criteria are imposed for diagnosis of PMDD: A diagnosis of PMDD requires the presence of at least five of these symptoms with one of the symptoms being number 1-4 (marked lability, irritability, depressed mood, anxiety and tension). These symptoms should occur during the week before menses and remit after initiation of menses. In order to meet criteria for the diagnosis, the symptoms should be charted prospectively for two consecutive ovulation cycles in order to confirm temporal and cyclical nature of symptoms. The symptoms should also be severe enough to affect normal work, school, or social activities or relationships with others.

It will be noted that menopause, the cessation of menstruation in a female mammal due to reduction and eventual cessation of estrogen production by the ovaries, and premenopause and perimenopause, the period of life of a female mammal during which signs and symptoms of menopause begin to appear and increase, are often accompanied by both somatic and behavioral/emotional symptoms similar to those characteristic of menstrual cycle-induced symptoms (e.g. mood swings, weight gain, diminished libido, sleep disturbance, fatigue, headache). Pre- and perimenopause are also frequently accompanied by intensification of the severity of PMS, PMDD, menstrual dysphoria and dysmenorrhea. Another common premenopausal, perimenopausal and menopausal symptom is migraine. Currently available remedies for symptoms of menopause and pre- and perimenopause are also similar to those commonly prescribed for menstrual cycle-induced symptoms (e.g. hormone therapy, antidepressant drugs, NSAIDS, pain medication, acupuncture, herbal supplements). Thus, application of the methods, compositions and kits of the instant invention for treatment of women suffering from somatic and behavioral/emotional symptoms of pre- and perimenopause, and for menopause itself, is also envisioned.

Thus, in some embodiments, the subject is a female mammal, suffering from PMS, PMDD, a perimenstrual disorder or another menstrual cycle-associated condition. In particular embodiments, the subject is a female human.

As used herein, the phrase "menstrual cycle" refers to the monthly cycle of changes in the ovaries and the lining of the uterus (endometrium). The four phases of the menstrual cycle are menstruation (menses), follicular phase, ovulation and the luteal phase.

Menstruation is the elimination of the thickened lining of the uterus (endometrium) from the body. Average length of menstruation (menses) is between three days and one week. In some embodiments, menstruation can be fewer than three days or longer than one week, up to two weeks or more.

The follicular phase begins with onset of menses and ends with ovulation, and is characterized by release of hormones stimulating follicle production and endometrial thickening. Ovulation is the rupture of the follicle and release of a mature egg from the ovarian surface, stimulated by Luteinizing Hormone (LH). Ovulation typically occurs at mid-cycle, or day 14 of a 28 day menstrual cycle, although this can vary among individuals. The released egg is transported to the uterus in preparation for fertilization.

Luteal phase: During ovulation, the egg is released from the follicle, but the ruptured follicle transforms into a glandular structure (corpus luteum) secreting progesterone and estrogen, for maintenance of the endometrium in anticipation of fertilization and implantation. Unless fertilization occurs, the cycle ends with the corpus luteum withering, usually around day 22 of a 28 day cycle. The drop in progesterone then causes shedding of part of the endometrium, which is menstruation (menses). As used herein, the beginning of the menstrual cycle, designated as "day 1" of the menstrual cycle, is the day of onset of menses.

Although there exists variance among individuals, a typical menstrual cycle in human females is 28 days. In other embodiments, the cycle is 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days or up to 40 days. In some embodiments, the menstrual cycle of the subjects is irregular, some months being about 28 days, other months being fewer than 28 days from onset of menses to onset of menses, and/or in other months being greater than 28 days from the onset of menses to onset of menses. In some embodiments, the menstrual cycle of the subjects is between 24 to 38 days.

According to some aspects of the present invention, the menstrual cycle-induced symptom(s) can occur at any one of the four phases of the menstrual cycle. In particular embodiments, the menstrual cycle-induced symptom(s) occur during the luteal phase and/or at the onset of menses and a few (1-3, 1-5, 1-7) days after onset of menses.

In some embodiments, the at least one menstrual cycle-induced symptom is expected to occur, or has occurred prior to the onset of menses. In some embodiments, the menstrual cycle-induced symptom(s) is expected to occur between 1-15 days, between 1-7 days, between 1-10 days prior to onset of menses. In other embodiments, the menstrual cycle-induced symptom(s) is expected to occur or has occurred 1, 2, 3, 4, 5, 6, 7, 8, 9, 10, 11, 12, 13, 14 or 15 days prior to onset of menses. In particular embodiments, the menstrual cycle-induced symptom(s) are expected to occur, or have occurred 3-7 days prior to the onset of menses.

In some embodiments, the at least one menstrual cycle-induced symptom is expected to occur, or has occurred following the onset of menses. In some embodiments, the menstrual cycle-induced symptom(s) is expected to occur between 1-7 days, between 1-10 days following the onset of menses. In other embodiments, the menstrual cycle-induced symptom(s) is expected to occur or has occurred 1, 2, 3, 4, 5, 6, 7, 8, 9, 10, 11, 12, 13, 14 or 15 days following onset of menses. In particular embodiments, the menstrual cycle-induced symptom(s) are expected to occur, or have occurred 2, 3, 4, 5 or 6 days following onset of menses.

In some embodiments, the symptom(s) is expected to occur, or have occurred between 1-7 days prior to and 1-7 days following the onset of menses (day −7 to day +7). In particular embodiments, the menstrual cycle-induced symptom(s) are expected to occur, or have occurred between day −5 to day +5 of the menstrual cycle, day −4 to day +5 of the menstrual cycle, day −3 to day +4 of the menstrual cycle, day −2 to day +3 of the menstrual cycle and day −1 to day +4 of the menstrual cycle.

It will be noted that the repetitive nature of menstrual cycle-induced symptoms provides the opportunity for a subject suffering from such menstrual cycle induced symptoms to anticipate the onset of these symptom(s) and obtain relief via administration of 3-MMC prior to the symptoms' onset. The present inventors have observed that administration of 3-MMC in anticipation of menstrual cycle-induced symptoms can significantly reduce the intensity as well as duration of many menstrual cycle induced symptoms and improve the women's quality of life during the perimenstrual period. Thus, in some embodiments, administering of 3-MMC occurs prior to the time at which the menstrual cycle-induced symptom(s) is expected to occur. In some embodiments, administering of 3-MMC occurs 1-5 days, 1-4 days, 1-3 days, 1-2 days, 5, 4, 3, 2 or 1 day prior to the time at which the menstrual cycle-induced symptom(s) is expected to occur. In other embodiments, administering of 3-MMC occurs 48 hours, 40 hours, 36 hours, 32 hours, 28 hours, 24 hours, 18 hours, 12 hours, 10 hours, 9 hours, 8 hours, 7 hours, 6 hours, 5 hours, 4.5 hours, 4 hours, 3.5 hours, 3 hours, 2.5 hours, 2 hours, 1.5 hours, 1 hour, 45 minutes, 30 minutes or 15 minutes prior to the time at which the menstrual cycle-induced symptom(s) is expected to occur.

The present inventors have also observed significant positive effects of 3-MMC when administered when symptoms are expected to occur, or have occurred. Further, some subjects reported that 3-MMC was effective even when administered after the onset of menstrual cycle-induced symptoms.

Thus, in some embodiments, administering of 3-MMC occurs 1-5 days, 1-4 days, 1-3 days, 1-2 days, 1, 2, 3, 4 or 5 days following onset of the menstrual cycle-induced symptom(s). In other embodiments, administering of 3-MMC occurs 1 hour, 2 hours, 3 hours, 4 hours, 5 hours, 6 hours, 7 hours, 8 hours, 10 hours, 12 hours, 16 hours, 18 hours, 24 hours, 28 hours, 36 hours or 40 hours following the time at which the menstrual cycle-induced symptom(s) has occurred (onset of menstrual cycle induced symptom).

3-MMC can be administered in a single administration, or can be administered in a regimen of repeated administration to the subject. The present inventors have observed a cumulative effect of repeated doses of 3-MMC, and in some cases, a persistent. In some embodiments, 3-MMC is administered repeatedly, at intervals of between 1-12 hours, between 1-2 days, between 1-4 days, between 1-6 days. In other embodiments, 3-MMC is administered repeatedly, at intervals of 1, 2, 3, 4, 5, 6, 7, 8, 9 or 10 hours between administrations.

In some embodiments, administration of 3-MMC is discontinued at the time at which the menstrual cycle-induced symptom(s) is relieved. In other embodiments, administration of 3-MMC is discontinued 1-7, 2-5, 3-6 or 4 days from the onset of menses. In specific embodiments, administration of 3-MMC is discontinued 1, 2, 3, 4, 5, 6 or 7 days or between 1-7 or 2-5 days from the conclusion of menses.

Although most of the subjects reported taking 3-MMC in anticipation of, or in response to mood and/or behavioral menstrual cycle-induced symptoms, some of the subjects reported alleviation of somatic symptoms previously experienced in association with their menstrual cycle. Thus, in some embodiments, the at least one menstrual cycle-induced symptom is a mood and/or behavioral symptom. In specific embodiments, the mood or behavioral symptom is selected from the group consisting of lethargy, eating disorders, forgetfulness, sleep disturbances, appetite changes, poor concentration, decreased interest, social withdrawal, irritability, mood swings, anxiety, tension, depression and feelings of lack of control.

A non-limiting list of suitable instruments for diagnosing, monitoring and evaluating subjects' menstrual cycle-induced symptoms, and changes therein prior to, during or following therapy using the methods of the present invention is provided in Table I:

TABLE I

| MONITORING AND OUTCOME MEASURES | | |
|---|---|---|
| Objective | Measure | Link/Info |
| Depression | PROMIS Emotional Distress - Depression (used by VIDUS) | 2008 PROMIS Health Organization and PROMIS Cooperative Group |
| | Centre for Epidemiologic Studies Depression Scale | National Institutes of Mental Health, US |
| | Beck's Depression Inventory | |
| | Hamilton Depression Rating Scale | |
| | Quick Inventory of Depressive Symptomology | Rush et al, Biol Psychiatry (2003) 54: 573-83. |

TABLE I-continued

MONITORING AND OUTCOME MEASURES

| Objective | Measure | Link/Info |
|---|---|---|
| Anxiety | PROMIS Emotional Distress - Anxiety (used by VIDUS) | PROMIS Item Bank v1.0 - Emotional Distress - Anxiety - Short Form 8a |
| | State-Trait Anxiety Inventory | Speilberger et al. Mind Garden Redwood CA |
| | Beck's Anxiety Inventory | Beck, A. T., Epstein, N., Brown, G., Steer, R. A. (1988). An inventory for measuring clinical anxiety: Psychometric properties. Journal of Consulting and Clinical Psychology, 56, 893-897. |
| | Hamilton Anxiety Rating Scale | Hamilton M. The assessment of anxiety states by rating. Br J Med Psychol 1959; 32: 50-55. |
| Mood | Profile of Mood States Questionnaire | Top End Sports and McNair et al. (1971) Manual for the Profile of Mood States. San Diego, CA: Educational and Industrial Testing Service. Grove, J. R., & Prapavessis, H. (1992). Preliminary evidence for the reliability and validity of an abbreviated Profile of Mood States. International Journal of Sport Psychology, 23, 93-109. |
| Self-Compassion | Self-Compassion Scale (Short Form) | 2011, Raes et al, Clin Psych Psychother 18 250-255 |
| Spiritual Dimensions | Persisting Effects Questionnaire | See above (also has items on depression & anxiety) |
| | Spirituality Index of Well Being | Daaleman, T. P. & Frey, B. B. (2004). The Spirituality Index of Well-Being: A new instrument for health-related quality of life research. Annals of Family Medicine, 2, 499-503. |
| | Strength of Religious Faith Questionnaire | Used in Hendricks protocol. |
| | Meaning in Life Questionnaire | Steger, M. F., Frazier, P., Oishi, S., & Kaier, M. (2006). The Meaning in Life Questionnaire: Assessing the presence of and search for meaning in life. Journal of Counseling Psychology, 53, 80-93. |
| | Satisfaction with Life Scale | Diener, E., Emmons, R. A., Larsen, R. J., & Griffin, S. (1985). The Satisfaction with Life Scale. Journal of Personality Assessment, 49, 71-75 |
| | ASPIRES Spiritual Transcendence Scale | See Bogenschutz protocol, by Bogenschutz et al 2015, and by Griffiths et al 2006. |
| | Brief Multidimensional Measure of Religiousness/Spirituality | See: Fetzer Institute, National Institute on Aging Working Group: Multidimensional Measurement of Religiousness, Spirituality for Use in Health Research. A Report of a National Working Group. Supported by the Fetzer Institute in Collaboration with the National Institute on Aging. Kalamazoo, MI: Fetzer Institute, 2003 (1999) and Research on Aging: "Measuring Multiple Dimensions of Religion and Spirituality for Health Research," Ellen L. Idler, Marc A. Musick, Christopher G. Ellison, Linda K. George, Neal Krause, Marcia G. Ory, Kenneth I. Pargament, Lynda H. Powell, Lynn G. Underwood, David R. Williams, 2003, 25: 4. |

In specific embodiments subjects' progress prior to, during or following therapy for menstrual cycle-induced symptoms using the methods of the present invention is evaluated using at least one of the Beck Depression Inventory, the Beck Anxiety Inventory, the Beck Hopelessness Scale, for PMDD: DSM V.

In other embodiments, the at least one menstrual cycle-induced symptom is a somatic symptom. Such somatic symptoms include, but are not limited to breast tenderness or swelling, joint or muscle pain, a sensation of 'bloating', headache, weight gain and abdominal cramps.

Most of the subjects reported that 3-MMC provided relief from more than one of the reported menstrual cycle-induced symptoms. Thus, in some embodiments, the at least one menstrual cycle-induced symptoms comprises at least two or more symptoms (see supra for partial list of characteristic symptoms). In some embodiments, the at least one menstrual cycle-induced symptom comprises two or more of depression, lethargy, irritability, anxiety, social withdrawal and mood swings.

It will be appreciated that, in some embodiments, the subject may be suffering from more than a single menstrual cycle-induced symptom. In the event of multiple symptoms, the methods of treating of the present invention may be directed to treatment of a single symptom among the multiple symptoms, according to priorities determined by a therapist and/or subject, or, in some embodiments, it may be suitable to treat more than a single symptom concomitantly.

3-MMC is effective for relief of menstrual cycle-induced symptoms over a range of concentrations.

In some embodiments, a therapeutically effective amount of 3-MMC is administered to the subject. In some embodiments, 3-MMC is administered to the subject in an amount in the range of 5 mg to 1000 mg per administration. In some embodiments, 3-MMC is administered to the subject in an amount in a range of approximately 7 mg to approximately 950 mg per administration, approximately 7 mg to approximately 950 mg per administration, approximately 10 mg to approximately 900 mg per administration, approximately 15 mg to approximately 850 mg per administration, approximately 20 mg to approximately 800 mg per administration, approximately 25 mg to approximately 780 mg per administration, approximately 30 mg to approximately 750 mg per administration, approximately 35 mg to approximately 700 mg per administration, approximately 40 mg to approximately 650 mg per administration, approximately 45 mg to approximately 600 mg per administration, approximately 50 mg to approximately 550 mg per administration, approximately 52 mg to approximately 500 mg per administration, approximately 57 mg to approximately 480 mg per administration, approximately 60 mg to approximately 450 mg per administration, approximately 63 mg to approximately 430 mg per administration, approximately 70 mg to approximately 400 mg per administration, approximately 75 mg to approximately 370 mg per administration, approximately 77 mg to approximately 350 mg per administration, approximately 80 mg to approximately 330 mg per administration, approximately 85 mg to approximately 300 mg per administration, approximately 90 mg to approximately 280 mg per administration, approximately 95 mg to approximately 250 mg per administration, approximately 100 mg to approximately 230 mg per administration, approximately 105 mg to approximately 200 mg per administration, approximately 110 mg to approximately 190 mg per administration, approximately 115 mg to approximately 175 mg per administration, approximately 120 mg to approximately 165 mg per administration, approximately 125 mg to approximately 160 mg per administration or approximately 130 mg to approximately 155 mg per administration. In some embodiments, 3-MMC is administered to the subject in an amount in a range of 20 mg to 500 mg, 22 mg to 490 mg, 27 mg to 470 mg, 30 mg to 450 mg, 33 mg to 435 mg, 40 mg to 410 mg, 47 mg to 390 mg, 50 mg to 375 mg, 55 mg to 360 mg, 57 mg to 350 mg, 60 mg to 320 mg, 63 mg to 300 mg, 67 mg to 290 mg, 70 mg to 270 mg, 75 mg to 260 mg, 77 mg to 250 mg, 80 mg to 240 mg, 85 mg to 220 mg, 90 mg to 210 mg or 100 mg to 200 mg per administration. It will be appreciated that each individual range of amount of 3-MMC administered represents a single, separate embodiment.

In some embodiments, 3-MMC is administered to the subject in an amount of 5, 10, 12.5, 15, 17.5, 20, 22.5, 25, 27.5, 30, 32.5, 35, 37.5, 40, 42.5, 45, 47.5, 50, 52.5, 55, 57.5, 60, 62.5, 65, 67.5, 70, 73, 75, 77, 80, 83, 85, 87, 90, 93, 95, 97, 100, 103, 107, 110, 113, 115, 117, 120, 123, 125, 127, 130, 133, 137, 140, 143, 145, 147, 150, 153, 155, 157, 160, 163, 167, 170, 173, 175, 177, 180, 183, 185, 187, 190, 193, 195, 197, 200, 220, 240, 250, 275, 290, 300, 310, 320, 330, 340, 350, 360, 370, 380, 390 or 400 mg per administration. In particular embodiments, 3-MMC is administered in an amount of 12.5 mg per administration, 25 mg per administration, 35 mg per administration, 50 mg per administration or 60 mg per administration. In specific embodiments, 3-MMC is administered in an amount of 25 mg per administration.

In some embodiments, 3-MMC is administered to the subject in a dosage calculated according to mass per body weight, e.g. mg 3-MMC per Kg body weight of the subject. In some embodiments, 3-MMC is administered to the subject in a dosage range of approximately 0.1 to approximately 1 mg/Kg body weight per administration, approximately 0.5 mg/Kg to approximately 7 mg/Kg body weight per administration, approximately 0.75 mg/Kg to approximately 6.5 mg/Kg body weight per administration, approximately 1.0 mg/Kg to approximately 6.0 mg/Kg body weight per administration, approximately 1.25 mg/Kg to approximately 5.5 mg/Kg body weight per administration, approximately 1.5 mg/Kg to approximately 5 mg/Kg body weight per administration, approximately 1.75 mg/Kg to approximately 4.5 mg/Kg body weight per administration, approximately 2.0 mg/Kg to approximately 4.25 mg/Kg body weight per administration, approximately 2.25 mg/Kg to approximately 4.0 mg/Kg body weight per administration, approximately 2.5 mg/Kg to approximately 3.75 mg/Kg body weight per administration, approximately 2.75 mg/Kg to approximately 3.5 mg/Kg body weight per administration body weight per administration. It will be appreciated that each individual range of 3-MMC per Kg body weight administered represents a single, separate embodiment.

In some embodiments, 3-MMC is administered to the subject in a dosage of 0.1, 0.2, 0.3, 0.4, 0.5, 0.75, 1.0, 1.25, 1.5, 1.75, 2.0, 2.25, 2.5, 2.75, 3.0, 3.25, 3.5, 3.75, 4.0, 4.25, 4.5, 4.75, 5.0 or 5.5 mg/Kg body weight per administration. In specific embodiments, 3-MMC is administered to the subject in a dosage of 0.1, 0.2, 0.3, 0.4, 0.5, 1, 1.5, 2, 2.5 or 3 mg/Kg body weight per administration.

3-MMC can be administered to the subject via methods including, but not limited to oral administration, intravenous administration, insufflation (nasal administration), mucosal administration, rectal administration, transdermal administration and inhalation (e.g. dry powder or vapor inhalation). In specific embodiments of the method of the invention, the 3-MMC is administered to the subject via oral administration. In particular embodiments, 3-MMC is administered orally to the subject in an amount of 10 mg per administration, 12.5 mg per administration, 25 mg per administration, 35 mg per administration, 50 mg per administration, 100 mg per administration, 150 mg per administration, 200 mg per administration, 250 mg per administration, 300 mg per administration, 350 mg per administration or 400 mg per administration.

In some embodiments, consecutive doses of 3-MMC can be administered using equal amounts (e.g. 2 or more doses of 12.5 or 25 or 35 mg) per dose. In other embodiments, amounts of 3-MMC can be ramped up between doses (e.g. first dose of 12.5 mg followed by 25 mg, finally reaching 35 or 50 mg 3-MMC), or tapered between doses (e.g. first dose of 35 or 50 mg, followed by 25 mg, finally reaching 12.5 or 10 mg 3-MMC). In specific embodiments, consecutive doses of 3-MMC for menstrual cycle-induced symptoms are administered once or twice at 25 mg, followed by doses of 12.5 mg.

Safety and pharmacokinetic studies with animal models have indicated that peak serum concentrations of 3-MMC are apparent within 5-10 minutes after oral administration, and that the apparent plasma half-life, after oral ingestion, is approximately 0.8 hours. The present inventors have observed that, in some embodiments the onset of human subject's perception of 3-MMC's effect is approximately 30-90 minutes following oral administration, varying according to whether the 3-MMC was administered to a fasting subject (more rapid onset), or following a meal (less rapid onset). In some cases, the perception of peak effect of 3-MMC in human subjects occurs between 10 to 30 minutes after the initial perception of onset of 3-MMC's effect. The present inventors further observed that, for some subjects, the duration of perception of the effect of 3-MMC in human subjects was, in most cases, for no greater than 6-8 hours following oral administration.

Thus, in some embodiments, the 3-MMC is administered at least twice for menstrual cycle-induced symptoms. In some embodiments, the 3-MMC is administered twice for menstrual cycle-induced symptoms, at intervals of 1-12 hours between dosings. In other embodiments, the 3-MMC is administered twice or three times for menstrual cycle-induced symptoms, at intervals of 2-8 hours between dosings. In other embodiments, the 3-MMC is administered twice or three times for menstrual cycle-induced symptoms, at intervals of 3-6 hours between dosings. In other embodiments, the 3-MMC is administered twice or three times for menstrual cycle-induced symptoms, at intervals of 1-4 hours between dosings. In other embodiments, the 3-MMC is administered twice or three times for menstrual cycle-induced symptoms, at intervals of 1-3 hours between dosings. In yet other embodiments, the 3-MMC is administered twice or more for menstrual cycle-induced symptoms, at intervals of 1-2 hours between dosings.

In some embodiments, 3-MMC is administered in multiple doses (e.g. more than once), where each administration is of the same dosage of 3-MMC (e.g. 3×25 mg, 2×25 mg, 2×12.5 mg, and the like). In other embodiments, 3-MMC is administered in multiple doses (e.g. more than once) for menstrual cycle-induced symptoms, where each administration is of a different dosage of 3-MMC (e.g. 1×12.5 mg followed by 1×25 mg; 1×25 mg followed by 1×12.5 mg, followed by a third dose of 1×12.5 mg; 1×12.5 mg, followed by 1×50 mg, and the like). Combinations of initial higher and subsequent lower doses, as well as combinations of initial lower, and subsequent higher doses, as well as subsequent dosages alternating between lower and higher than the initial dose are also envisioned.

It will be appreciated that the method of the present invention can be combined with other therapeutic modalities. Pharmacotherapy is a common treatment approach to menstrual cycle-induced symptoms. Thus, in some embodiments, the subject is being treated with at least one drug selected from the group consisting of selective serotonin re-uptake inhibitors (SSRIs), mono-amine-oxidase (MAO) inhibitors, serotonin-dopamine antagonists, analgesics, anti-hypertensive drugs, anti-allergenics, anxiolitics, anti-inflammatory drugs, oral contraceptives, nutritional supplements (e.g. calcium, vitamin B6, vitamin E, magnesium, L-tryptophan), chasteberry (agnus castus) and/or chasteberry extract, muscle relaxants and local anesthetics. In specific embodiments, the method of the present invention further comprises administering to the subject at least one drug selected from abovementioned group.

Yet further, non-pharmacological approaches have become popular recently, and can also be integrated within the methods of the present invention. Thus, in some embodiments, the method of the present invention further comprises exposing the subject to an adjunct therapeutic, non-pharmacological modality selected from the group consisting of, for example, at least one of music, exercise, acupuncture, visual stimulus, audio stimulus, thermal comfort, "bodywork" (e.g. massage, chiropractic).

The 3-MMC of some embodiments of the invention can be administered to a subject per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the 3-MMC accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

In some embodiments, the compositions may be formulated for control of release of the active ingredients. In some embodiments, the 3-MMC or composition thereof is formulated for "immediate release". As used herein, the term "immediate release" (IR) refers to a release of an active agent to an environment over a period of seconds to no more than about 30 minutes once release has begun and release begins within a second to no more than about 15 minutes after exposure to an aqueous environment. An immediate release composition, which does not possess a substantial delay in drug release, should be considered a subset of a rapid release composition. An immediate release composition releases drug in the buccal cavity, esophagus and/or stomach.

In some embodiments, the 3-MMC or composition thereof is formulated for "rapid release". As used herein, the term "rapid release" (RR) refers to a release of an active agent to an environment over a period of seconds to no more than about 59 minutes once release has begun and release can begin within a few seconds or minutes after exposure to an aqueous environment or after expiration of a delay period (lag time) after exposure to an aqueous environment. In general, a rapid release composition releases drug releases drug in the stomach, jejunum or duodenum after oral administration, provided the composition does not include a delayed release material or delayed release coating. In such a case, the rapid release composition would release drug in the upper, middle and/or lower intestine or colon.

In some embodiments, the 3-MMC or composition thereof is formulated for "extended release". As used herein, the term "extended release" (ER) refers to a controlled release of an active agent from a dosage form to an environment over (throughout or during) an extended period of time, e.g. greater than or equal to one hour. As used herein, the term "extended release" profile assumes the definition as widely recognized in the art of pharmaceutical sciences. An extended release dosage form will release drug at substantially constant rate over an extended period of time or a substantially constant amount of drug will be released incrementally over an extended period of time. The term "extended release", as regards to drug release, includes the terms "controlled release", "prolonged release", "sustained release", or "slow release", as these terms are used in the pharmaceutical sciences.

In some embodiments, the 3-MMC or composition thereof is formulated for "controlled release". As used herein, the term "controlled release" (CR) refers to a release of an active agent to an environment over a period of about eight hours up to about 12 hours, 16 hours, 18 hours, 20 hours, a day, or more than a day. A controlled release can begin within a few minutes after exposure to an aqueous environment or after expiration of a delay period (lag time) after exposure to an aqueous environment.

In some embodiments, the 3-MMC or composition thereof is formulated for "sustained release". As used herein, the term "sustained release" (SR) refers to a controlled release of an active agent to maintain a constant drug level in the blood or target tissue of a subject to which the pharmaceutical composition is administered.

For buccal administration, the compositions may take the form of tablets or lozenges formulated in conventional manner.

According to some embodiments, enteral coating of the composition is further used for oral or buccal administration. As used herein, the term "enteral coating" refers to a coating which controls the location of composition absorption within the digestive system. Non-limiting examples for materials used for enteral coating are fatty acids, waxes, plant fibers or plastics.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use. The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of 3-MMC effective to treat, prevent, alleviate or ameliorate symptoms of a menstrual cycle-induced disorder or condition in the subject.

Determination of a therapeutically effective amount is well within the capability of those skilled in the art, especially in light of the detailed disclosure provided herein.

For any preparation used in the methods of the invention, the therapeutically effective amount or dose can be estimated initially from animal models. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide levels of 3-MMC sufficient to induce or suppress the biological effect (minimal effective concentration, MEC). The MEC will vary for each preparation, but can be estimated from animal models. Dosages necessary to achieve the MEC will depend on individual characteristics and route of administration. Detection assays can be used to determine plasma concentrations.

As detailed hereinabove, depending on the severity and responsiveness of the condition to be treated, dosing can be of a single or a plurality of administrations, with course of treatment lasting from several days to several weeks or until cure is effected or diminution of the disorder or condition is achieved.

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit, which may contain one or more unit dosage forms containing 3-MMC as the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

Thus, according to some embodiments, there is provided a kit for use in treating at least one menstrual cycle-induced symptom in a subject comprising at least one unit dosage comprising a therapeutically effective amount of 3-methyl-methcathinone (3-MMC) and instructions for the use of 3-MMC before, during or following the time at which the menstrual cycle-induced symptom is expected to occur, or has occurred, and packaging material. Types of menstrual cycle-induced symptoms suitable for combination with administering 3-MMC according to the methods of the present invention are described in detail hereinabove. In some embodiments, the instructions indicate that the menstrual cycle induced symptom is a symptom of PMS in the subject. In other embodiments, the instructions indicate that the menstrual cycle induced symptom is a symptom of PMDD. In still other embodiments the instructions indicate that the menstrual cycle induced symptom is a symptom of a perimenstrual disorder or condition.

As noted above, the cyclic character of menstrual cycle-induced symptoms provides the opportunity for close approximation, or prediction of the time of onset of the symptoms, and thus pre-emptive administration of 3-MMC for treatment and relief of the symptoms. Thus, in some embodiments, the kit comprises specific unit dosages of 3-MMC with instructions for their administration at a designated time within the subject's menstrual cycle. Suitable timing of such pre-emptive or preventative administration of 3-MMC for menstrual cycle-induced symptoms is detailed above. Exemplary unit dosages of 3-MMC suitable for use with the kit of the present invention include between 5 and 100 mg, between 10 and 80 mg, between 12.5 and 75 mg, between 20 and 60 mg, between 25 and 50 mg 3-MMC. In specific embodiments, the unit dosage of the kit comprises 12.5, 15, 17.5, 20, 22.5, 25, 27.5, 30, 32.5, 35, 37.5, 40, 42.5, 45, 47.5, 50, 52.5, 55, 60, 65, 70, 75, 80, 90 or 100 mg 3-MMC. In particular embodiments, the unit dosage of the kit comprises 12.5 or 25 or 35 or 50 mg 3-MMC.

In one non-limiting example, the kit can comprise one, two or more unit dosages of 12.5, 25, 35 or 50 mg 3-MMC, with instructions for their administration 0.5-5 days prior to expected occurrence of the menstrual cycle-induced symptom, and packaging material. An exemplary kit of the invention may comprise instructions for administration of the unit dosage or dosages of 3-MMC on the day of expected occurrence of the menstrual cycle-induced symptom, expressed as n days counted from the previous onset of menses, where n is the characteristic interval from onset of menses to the at least one menstrual cycle-induced symptom. In some embodiments, the instructions indicate specific intervals or ranges of intervals between sequential administration of multiple unit dosages of 3-MMC. In further embodiments, the instructions indicate increase ("ramping") or decrease ("tapering") of the unit dosages for sequential administration of multiple unit dosages of 3-MMC. Suitable intervals between unit dosages are detailed above.

In some embodiments, in order to improve the accuracy of timing of administration of the 3-MMC, the kit further comprises a device for determining the time at which the at least one menstrual cycle-induced symptom is expected to occur in the subject. Thus, a subject suffering from menstrual cycle-induced symptom(s) can record the cyclic recurrence of the menstrual cycle-induced symptom(s) and adjust the timing of administration of 3-MMC unit dosage(s) accordingly. Still further, such a subject may record the response to previous administration or timing of administration of 3-MMC in order to better calibrate future timing and dosages of 3-MMC administration.

Such a device can be convention manual recording device, such as a chart, or it can be a digital recording device. Thus, in some embodiments, there is provided a kit of the invention, accompanied by a digital computer interface for recording chronology and character of the at least one menstrual cycle-induced symptom. Such a digital computer interface can allow manual input of the timing, duration, and character (e.g. severity) of the symptom, as well as parameters of the response to administration of 3-MMC. In some embodiments, the digital computer interface is of a cellular phone application ("app"), and the kit further comprises a barcode for downloading and/or activating the application. Suitable configurations of cellular phone applications and accompanying barcodes for activation and/or downloading are well known in the art.

It is expected that during the life of a patent maturing from this application many relevant methods for treating subjects suffering from menstrual cycle-induced symptoms with 3-MMC will be developed and the scope of the term "administering 3-MMC to a subject suffering from menstrual cycle-induced symptoms" is intended to include all such new technologies a priori.

Herein throughout, the term 3-MMC or 3-Methylmethcathinone encompasses a compound of the formula:

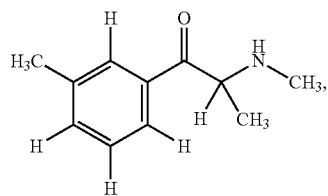

including deutorated forms thereof.

As used herein, the tern "deutorated form" of a compound describes a compound in which one or more of the hydrogen atoms are replaced by the deuterium isotope.

According to some of any of the embodiments described herein, the 3-MMC or a deuterated form thereof can be in a form of a pharmaceutically acceptable salt thereof.

As used herein, the phrase "pharmaceutically acceptable salt" refers to a charged species of the parent compound and its counter-ion, which is typically used to modify the solubility characteristics of the parent compound and/or to reduce any significant irritation to an organism by the parent compound, and/or to improve its stability, while not abrogating the biological activity and properties of the administered compound. A pharmaceutically acceptable salt of a compound as described herein can alternatively be formed during the synthesis of the compound, e.g., in the course of isolating the compound from a reaction mixture or re-crystallizing the compound.

In the context of some of the present embodiments, a pharmaceutically acceptable salt of the 3-MMC described herein may optionally be an acid addition salt comprising a protonated amine in combination with at least one counter-ion, derived from the selected acid, that forms a pharmaceutically acceptable salt.

The acid addition salts of the compounds described herein may therefore be complexes formed between the amine group of the compound and one or more equivalents of an acid.

An acid addition salt of 3-MMC is typically a mono-addition salt.

The phrase "mono-addition salt", as used herein, refers to a salt in which the stoichiometric ratio between the counter-ion and charged form of the compound is 1:1, such that the addition salt includes one molar equivalent of the counter-ion per one molar equivalent of the compound.

The acid addition salts may include anions derived from a variety of organic and inorganic acids, such as, but not limited to, hydrochloric acid which affords a hydrochloric acid addition salt, hydrobromic acid which affords a hydrobromic acid addition salt, acetic acid which affords an acetic acid addition salt, ascorbic acid which affords an ascorbic acid addition salt, benzenesulfonic acid which affords a besylate addition salt, camphorsulfonic acid which affords a camphorsulfonic acid addition salt, citric acid which affords a citric acid addition salt, maleic acid which affords a maleic acid addition salt, malic acid which affords a malic acid addition salt, methanesulfonic acid which affords a methanesulfonic acid (mesylate) addition salt, naphthalenesulfonic acid which affords a naphthalenesulfonic acid addition salt, oxalic acid which affords an oxalic acid addition salt, phosphoric acid which affords a phosphoric acid addition salt, toluenesulfonic acid which affords a p-toluenesulfonic acid addition salt, succinic acid which affords a succinic acid addition salt, sulfuric acid which affords a sulfuric acid addition salt, tartaric acid which affords a tartaric acid addition salt and trifluoroacetic acid which affords a trifluoroacetic acid addition salt.

The present embodiments further encompass any enantiomers, diastereomers, prodrugs, solvates, hydrates of the 3-MMC (or a deuterated form thereof).

As used herein, the term "enantiomer" refers to a stereoisomer of a compound that is superposable with respect to its counterpart only by a complete inversion/reflection (mirror image) of each other. Enantiomers are said to have "handedness" since they refer to each other like the right and left hand. Enantiomers have identical chemical and physical properties except when present in an environment which by itself has handedness, such as all living systems. In the context of the present embodiments, 3-MMC or a deuterated form thereof may exhibit one or more chiral centers, each of which exhibiting an R- or an S-configuration and any combination.

The term "diastereomers", as used herein, refers to stereoisomers that are not enantiomers to one another. Diastereomerism occurs when two or more stereoisomers of a compound have different configurations at one or more, but not all of the equivalent (related) stereocenters and are not mirror images of each other. When two diastereoisomers differ from each other at only one stereocenter they are epimers. Each stereo-center (chiral center) gives rise to two different configurations and thus to two different stereoisomers. In the context of the present invention, embodiments of the present invention encompass compounds with multiple chiral centers that occur in any combination of stereo-configuration, namely any diastereomer.

The term "prodrug" refers to an agent, which is converted into the active compound (the active parent drug) in vivo. Prodrugs are typically useful for facilitating the administration of the parent drug. They may, for instance, be bioavailable by oral administration whereas the parent drug is not. A prodrug may also have improved solubility as compared with the parent drug in pharmaceutical compositions. Prodrugs are also often used to achieve a sustained release of the active compound in vivo.

The term "solvate" refers to a complex of variable stoichiometry (e.g., di-, tri-, tetra-, penta-, hexa-, and so on), which is formed by a solute (the compound of the present invention) and a solvent, whereby the solvent does not interfere with the biological activity of the solute. Suitable solvents include, for example, ethanol, acetic acid and the like.

The term "hydrate" refers to a solvate, as defined hereinabove, where the solvent is water.

It is expected that during the life of a patent maturing from this application relevant forms of 3-MMC (e.g., purified enantiomers, deuterated forms, salts, etc.) will be developed and the scope of the term "3-MMC" is intended to include all such new technologies a priori. a As used herein the term "about" or "approximately" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion. Generally, the nomenclature used herein includes medical, pharmacological and pharmaceutical techniques. Such techniques are thoroughly explained in the literature. See, for example, the DSM-V and the ICD 10, both of which are incorporated by reference as if fully set forth herein. Other general references are provided throughout this document. The procedures therein are believed to be well known in the art and are provided for the convenience of the reader. All the information contained therein is incorporated herein by reference.

The following case studies exemplify some aspects of some embodiments of the methods of the present invention for treating perimenstrual disorders in subjects suffering at least one menstrual cycle-induced symptom by administering 3-MMC.

Closed Label Trials of 3-MMC for Menstrual Cycle-Induced Symptoms

Detailed reports of 11 experiences of women with unlabeled ("pill") 3-MMC for menstrual cycle-induced symptoms.

Example I: "Gertie"

Gertie is a 41 year old Dutch woman, (1.70 m. 57 kg.) who had previously unstructured experience with 3-MMC in relation to the alleviation of menstrual-induced symptoms (mostly PMS), using 3-MMC on different occasions and during the previous year. Due to her account and positive experience the trial was initiated to confirm the positive effects of 3-MMC on other women regarding menstrual-induced symptoms.

Gertie is in a stable relationship, with four children. Apart from being a mother, she is a business-woman with multiple activities and responsibilities, a busy mother but with no underlying health issues other than suffering from moderate to severe PMS symptoms in the last two years, especially following cessation of oral contraceptives.

Menstrual Cycle-Induced Symptoms

Usual acknowledged PMS symptoms; Gertie often or very often suffers from:

Emotional distress (last two years)
Irritability/being upset (last two years)
Tension (last two years)
Feeling alone/helplessness (last two years)
Oversensitive (last two years)
Indecisive (last two years)
Difficulty concentrating (last two years)

Looking for discussion and arguing (last two years)
Interpersonal conflicts (lately)

Background

Gertie used oral contraceptives until she was 38 years old. After discontinuing oral contraceptives, and for the last two years, she has became more and more aware of the menstrual-induced symptoms, and gradually increasing severity of her PMS distress. During the days before Gertie's period she experiences a stronger need to be around other people and to have company, perhaps for distraction from the distress of the PMS.

Onset of Gertie's PMS symptoms is one or two days before her period, and experienced as a very challenging experience, making it harder to cope with work, family and children. Gertie's PMS also makes it difficult to enjoy weekends or free days.

Gertie is very open, talks frankly about her period and her PMS. As she feels that loneliness is part of the problem, so sharing with other people helps her.

Gertie's PMS causes argumentativeness and agitation, heightening the consciousness of her conditions. Somehow the awareness of her menstrual cycle makes her more observant and closer to her feelings. Gertie is conscious that her menstrual-induced tension is recurring, monthly, is aware of increased irritability and knows when to alleviate her anxiety.

Gertie has experimented with different doses of 3-MMC for PMS over approximately two years, approximately 20 times for 15 menstrual periods.

Dosage

Gertie has been trying the 3-MMC on steady basis for her last fifteen menstrual periods; she usually takes only one or two pills a couple of days before her menstruation. Having experimented with doses greater and lesser than 25 mg, Gertie has concluded that a dose between 20 and 25 mg is most effective for her.

Motivation

On the many occasions Gertie decided to take the pill she was feeling particularly distressed, usually at the start of the day when she is feeling irritable "with no reason", prone to initiate a discussion. She especially feels uncomfortable with interpersonal connections, is indecisive, anxious and lonely. Heartfelt discussion of her feelings looms as a difficult task.

Dosage and Regimen

Gertie usually takes the pill in the morning, after breakfast and before lunch because it is at that time of the day that she can already foresee a difficult day.

She has been trying different doses. She didn't perceive any benefit with doses between 10 mg and 20 mg. She felt positive effects with doses between 20 and 30 mg. She has tried 40 mg. in one intake, but she considers it is a bit too much; she never tried a higher dose than that.

Pharmacodynamics

Gertie starts feeling an effect after half an hour to one hour; she acknowledges that the peak moment of a desired effect is between one hour and a half and two hours. After four hours the effect starts to fade away and after six hours it is gone.

Response

Gertie feels less tense and that is perceived in the way she breathes. She can breathe better and more easily-when she is agitated, the oxygen "doesn't sink down in her body", and with the pill she can take big deep breaths.

Psychological Effects

Gertie feels "back to normal" (like on the days without PMS), she is able to take decisions again. It is as if her mind has "cleared up", the feeling before the pill as if there is a state of confusion and not being able to make up her mind. After the pill she is not necessarily more focused than usual, but just more comfortable with herself. Gertie doesn't feel like crying anymore and can better interact or get into an interpersonal relationship. She feels more stable.

Side Effects

She says that she never perceived non-desired side-effects, however there can be a relationship between pill intake and body temperature, feeling a bit hotter than normal and some changes in her appetite.

Example II—"Ana"

Ana is a 25 year old healthy female, (68 kg, 1.78 m) from Estonia. Ana works part time and is also a university student. She lives alone but she is in a relationship, she takes oral contraceptives, has never been pregnant and her menstrual periods are regular.

Menstrual Cycle-Induced Symptoms

Ana has reported physical and emotional complaints in relation to her menstrual period. Her menstrual cycle-induced symptoms usually last two or three days before her bleeding but she still feels the symptoms the first days of her menstruation which usually lasts up to seven days.

Usual acknowledged menstrual cycle-induced symptoms: Ana suffers chronically from:
  Acute oversensitivity (at least for the last eight years)
  Eating disorder/craving (at least for the last eight years)
  Acting out behavior (at least for the last eight years)
  Crying jags (for no reason) (at least for the last eight years)
  Feeling out of control (at least for the last eight years)
  Mood swings (at least for the last five years)
  Emotional distress (at least for the last five years)
  Feeling down (at least for the last five years)
  Irritability/being upset (at least for the last five years)
  Exhausted and tired (at least for the last five years)
  Lethargy/tiredness (at least for the last five years)
  Decreased interest in usual activities (at least for the last five years)

Less frequent symptoms (sometimes) but present through the years:
  Restlessness or nervous (in the last eight years)
  Forgetfulness (in the last eight years)
  Confusion (in the last eight years)
  Indecision (in the last eight years)
  Sleeping difficulties (in the last eight years)
  Anxiety (for the last five years)
  Tension (for the last five years)
  Loneliness/helplessness (for the last five years)
  Depression (for the last five years)
  Impatience (for the last five years)

Background

Ana got her menarche when she was 16 years old, and at that time she did not experience stress or pain, and neither in the years to follow. Serious symptoms commenced when she was 19 years old. For Ana it is very difficult to handle her menstrual cycle-induced symptoms and the same applies to her sister who also suffers from PMS (however their mother doesn't have any complaints).

All-in-all, the symptoms make Ana feel insecure, moody and craving food. The symptoms present her with a dilemma: she wants to be alone but she also longs for company. This puts some stress on her relationship: she wants to be close to her boyfriend but at the same time she underestimates herself during those days. Ana may feel ugly, not feminine enough, bloated and miserable. Ana does not believe that oral contraceptives can have an influence on her moodiness, since she still suffers from the symptoms even when she discontinues the oral contraceptives.

Ana sometimes even skips school or work due to the severity of her symptoms. She has been taking painkillers and has also tried other homeopathic remedies to ease her physical discomfort, but she feels that they don't really work. She has never discussed her emotional problems with a physician. Ana assumes that her menstrual cycle-induced symptoms is a "personal issue", to be dealt with solely by herself, and that there is no reason to either involve other people or use it as an excuse not to continue with a "normal life": a normal life that takes place when her pre- and menstruating days are over.

Summary

Ana is a healthy 25 year old young woman who suffers from moderate to severe menstrual cycle-induced symptoms. Ana's symptoms are compatible with PMS but also compatible with PMDD (dysphoria), due to the number of indicators and their duration in time.

Trial Period with 3-MMC

Duration 60 days with three menstrual periods in between—(second semester 2018)

Number of Trials

Three.

Trial I

Day of the menstrual period: first day of Ana's menstrual period

Main motivator for using the pill: physical pain and overall unrest/discomfort (scored the highest on her diary: emotional distress, mood swings, anxiety).

Time of the day: 7 pm in the evening, without food-fasting.

Dose: one dose of 25 mg.

Physical reaction: After one hour she already felt calmer and this feeling had its peak after two hours and remained like that for six hours. The pill didn't help to alleviate her stomach pain.

Psychological reaction: After one hour the emotional distress, mood swings and anxiety decreased.

After two hours Ana felt calmer and more relaxed, according to her this feeling lasted 24 hrs.

Side effects: none

Trial II

Day of the menstrual period: second day of her menstrual period

Main motivator for taking the pill: Scored high on her period calendar: emotional distress, feeling down, mood swings, helplessness, anxiety and nauseas.

Time of the day: First pill intake at 3 pm. Second pill intake at 8 pm.

Dose: two doses of 12.5 mg with an interval of five hours.

Physical reaction: After the first dose she was still feeling pain and uneasy for the first four hours so after that she decided to take a second dose that relieved her symptoms.

Psychological reaction: After the second dose she felt "mellow" and her emotional distress, feeling down, mood swings, helplessness and anxiety declined. The mellow feeling remained until she went to sleep.

Side effects: none

Trial III

Day of the menstrual period: last day of her menstrual period (one day before bleeding of her second month trial)

Main motivator for taking the pill: emotional distress and pain (the highest score on her diary was over sensitiveness, anger and sleeping difficulties)

Time of the day: First pill at 6 pm. Second pill intake at 11 pm.

Dose: two doses: one of 12.5 mg and the other of 25 mg. with an interval of five hours.

Physical reaction: after the first dose Ana felt the pain subside, her stomach pain seemed to fade away but she still felt a bit emotional.

Psychological reaction: After the second dose Ana experienced less emotional distress and felt much calmer. Two hours after the last dose she went to sleep. The higher dose 25 mg. proved to be beneficial at psychological level.

Side effects: Ana reported an outbreak of acne after her last dose (25 mg). Ana then discontinued use for fear of further acne.

Response:

A 12.5 mg dose had no effect on the subject, however a dose of 25 mg proved to be beneficial. The primary reason for administration was for physical, rather than emotional symptoms (self-reported). Ana reported experiencing relief in both physically and emotionally distressing situations: Ana noted that her physical pain was alleviated, and, on an emotional level, the 3-MMC made her feel calmer and more relaxed, relieving her moodiness, anxiety and nervousness.

The relaxed feeling start one hour after intake, with a highest peak after two hours, but Ana reported that the effect could last for a day or even a bit longer. Ana decided to discontinue administration of 3-MMC after taking 37.5 mg, associating it with a subsequent and unexplained episode of acne.

Example III:—"Bea"

Bea is a 21 year old female, (78 kilos, 1.73 m.), full time university student. Bea lives currently in the Netherlands, with other international roommates. Bea is an only child, far from her parents in Italy, her country of origin. She has a Dutch boyfriend, uses oral contraceptives and has never been pregnant. Bea does not use drugs or abuse any medication. She is a healthy young female with moderate-to-severe PMS symptoms that occur throughout most, but not all of her menstrual cycles.

Menstrual Cycle-Induced Symptoms

Bea often suffers from:

Moodiness (last three years)

Irritability/upset (since her menarche)

Exhaustion or fatigue (since her menarche)

Over sensitivity (since her menarche)

Lethargy (since menarche)

Crying jags (since menarche)

Less frequent symptoms:

Emotional distress (since her menarche)

Feeling down (last five years)

Depression (last six years)

Changes in the libido (last two years)

Background

Bea's symptoms have been rather strong and fluctuating over time since her menarche. Like other women studied, Bea pointed out that she noticed no relation between oral contraceptives and mood swings, because during the periods she of course discontinues the oral contraceptives but still perceives strong emotional distress. Bea reported that the same applies to her mother, who is very emotional during her period.

Bea's periods are regular; she tracks them ever since her gynecologist has asked her to pay attention to their periodicity, something that seems to help her understand how her feelings are related to her hormonal changes. Thus, Bea is very aware that the anticipation of her menstrual period interferes with the routines of her life. She is mostly troubled by her menstrual cycle-related symptoms one day before and the first two days of her menstruation: Bea feels quite irritable; she doesn't feel like doing anything (lethargic), especially in relation to her normal chores. Such as her university studies and other responsibilities. Bea also often experiences issues with deadlines, as she knows when the next menstruation will be coming, she has to adjust her study and any task deadlines relative to her period. Bea tries to get things done sooner because she is certain that her PMS will interfere with her performance on tasks. However, Bea recognizes she cannot always control external factors and sometimes will have to cope with responsibilities despite the sense of psychological and physical distress. For example, on the day of an important exam, Bea may feel annoyed (psychologically) or bloated and heavy (physically).

Therefore, the expectation of her monthly period puts stress and anxiety on her in both a conscious and unconscious manner. Bea, though, also recognizes that the distress caused by her period doesn't really have a significant impact on her social relations, although she does report occasional menstrual-cycle-related arguments with her boyfriend. Regardless of this, Bea makes an effort not to allow her period to interfere with her sentimental life. For the physical pain, Bea takes painkillers but she prefers if possible to avoid medication.

Summary:

Even though she has never been formally diagnosed with any defined menstrual cycle-induced condition, Bea meets the criteria for PMS. All the symptoms she experiences before her period are compatible with PMS and possibly even dysphoria (she has more than five) and she has been experiencing them regularly in time and for many years-sometimes the symptoms are from moderate to severe. In addition, Bea has acknowledged that the emotional distress associated with her period reduces her performance on both professional and study tasks.

Trial Period with 3-MMC

Duration

Two months, equivalent to three periods. Bea only took the pills during the one period, because she experienced extreme symptoms only then.

Number of Trials

Two

Trial I

Day of the menstrual period: third day of her menstrual period

Main motivator for taking the pill: Crying jags with no reason, over sensitivity, anxiety, tiredness, pain.

Time of the day: 9 am, After breakfast.

Dose: one pill of 12.5 mg.

Physical reaction: Before administration-fatigue. After the pill-less tired (started to feel the positive reaction after one hour and a half). After two hours Bea was definitely more alert. After six hours, physical pain was completely alleviated.

Psychological reaction: Bea felt more emotionally stable after one hour, less over-sensitive, less anxious and did not have episodes of crying for the rest of the day. The positive feelings lasted not only for the six hours following administration, but almost for the whole day.

Side effects: Bea perceived no negative physical reactions or side effects. She also took paracetamol for the pain and did not experience any undesirable interactions with the 3-MMC.

Trial II

Day of the menstrual period: day 15 of her menstrual period (time of ovulation)

Main motivator for taking the pill: Anger, irritability, emotional distress, confusion.

Time of the day: 10 am. After breakfast.

Dose: one dose of 25 mg.

Physical reaction: Before administration Bea reported feeling a "sort of drowsiness" that disappeared after one hour, leaving her feeling "normal" once again. The sense of "well-being" lasted a whole day.

Psychological reaction: Half an hour after administration Bea felt less angry and irritated. After approximately an hour and a half, she felt more in control and experienced abatement of her emotional distress and confusion. After two hours she started to feel really relaxed, a feeling that lasted for six hours. For the rest of the day she reported feeling "just stable".

Side effects: None

Response: Positive emotional distress relief with a minimum dose of 12.5 mg. With this dose Bea could already feel "stable" or back to normal. With a dose of 25 mg. she experienced a stronger effect of being more in control and relaxed. With the first trial, she was mainly relieved from a feeling of sadness; with the second administration relief from irritation and anger. Note that Bea only tried the pill during one menstrual period, because with the following period she experienced no symptoms for which she considered worth taking the pill. As can be inferred from her own account, she often suffers from distress during her periods, but not always.

Example IV: "Katy"

Katy is a 24 year old female, (58 kg, 1.70 m.) from the Ukraine, living with housemates/friends, is not in a relationship, does not use any form of contraception and has never been pregnant. Her menstrual periods are regular. She has always experienced severe physical and psychological symptoms associated with her period.

Menstrual Cycle-Induced Symptoms

Chronic symptoms:

Irritability (2 years)

Moodiness (2 years)

Emotional distress (2 years)

Impatience (2 years)

Over sensitiveness (2 years)

Anger (2 years)

Strong desire to be alone (2 years)

Desire to be silent (2 years)

Will to cry with no reason (2 years)

Altered libido (goes up during period)

Occasional symptoms:

Nervousness (2 years)

Tiredness

Depression (sometimes)

Feeling out of control

Physical problems and pain (headache, bloated, breast tenderness, etc.)

Background

Katy is a healthy person but in the past, a few years ago, she was diagnosed with depression and treated with antidepressants for half a year. The antidepressants were also intended to help her cope with the menstrual cycle-related moodiness she experiences. The antidepressants were not useful in her case and she decided to discontinue their use. However, Katy also acknowledged that, in general, she is not very sensitive to medication and that she often requires increased higher doses to achieve any positive effects.

Katy's menarche occurred when she was 11 years old, and she experienced no problems until she was 22 years old. One day, without warning, she realized that she was getting angry and upset around the time of her period. Since that time, Katy has related her mood to her menstrual cycle. Currently she experiences mood swings as early as a week before onset of menses. She also experiences a lot of pain during the first days of her period. Typically, the first night Katy will be woken and need to take painkillers, the second day the symptoms worsening and affecting her performance at work. Some days before her period Katy gets extremely irritated, she prefers to be alone and avoid any interaction. She acknowledges that her interaction problems are subjectively perceived, and her perception is that people are "slow" and she gets impatient. Her emotional distress began two years ago, severe pain and cramps beginning one year ago.

Around "those days", Katy prefers to be alone and deal with her issues on her own. However with close friends she is open and warns them in advance about her mood changes and her possible aggressive behavior, but at work she restrains herself and wears a "social mask". The physical pain she feels during the first days of her period makes her angry.

She is an only child and there is no information about whether her mother suffers/suffered from the same moodiness during her periods, as Katy is not very open about this topic with her mother.

Summary

Katy is a physically healthy young woman, who was previously diagnosed with depression, suffers from severe emotional and physical menstrual cycle-induced distress for the last two years. Her main symptoms are anger and irritability. She has tried antidepressants before, with no relief of the depression or the menstrual cycle-induced symptoms. Katy claims not to be very sensitive to medication.

Trial Period with 3-MMC

Duration 60 days with three menstrual periods in between—(second semester 2018)

Number of Trials

Seven

Trial I

Day of the menstrual period: 27th (one day before her next menstruation) Main motivator for taking the pill: Extreme irritability (also mood swings and emotional distress)

Time of the day: 11 am. After breakfast

Dose: one dose of 12.5 mg and one dose of 25 mg. (Total 37.5 mg.)

Physical reaction: After half an hour Katy perceived an accelerated heartbeat, after one hour slight dizziness, relaxation, "feeling high", which lasted for one more hour. Three hours after administration she felt hot and sweaty; her appetite diminished and remained that way the rest of the day.

Psychological reaction: After half an hour Katy became more self-conscious, concentrated. After one hour she was more willing to do things with an energetic flow that lasted up to four hours, then she was back to normal. However, in spite of the relaxing feeling, she could still sense anger and irritation, but now more in control.

Side effects: Accelerated heartbeat, dizziness, feeling hot and sweating.

Trial II

Day of the menstrual period: 28th or first day of her menstrual cycle

Main motivation for taking the pill: Extreme irritability and anger (also moodiness, tension and impatience)

Time of the day: 11:30 am. After breakfast

Dose: one dose of 12.5 mg plus one dose of 25 mg. (Total 37.5 mg)

Physical reaction: After half an hour Katy perceived slight acceleration of her heartbeat, after one hour she could still feel her heartbeat and perspiration (feeling sticky), these symptoms remained for two more hours, and then they faded away but a lack of appetite was perceived.

Psychological reaction: After one hour Katy felt much more energetic and willing to talk. She felt less irritated, less angry and more relaxed.

Side effects: Accelerated heartbeat, sweating and lack of appetite.

Trial III

Day of the menstrual period: 2nd day of her menstrual cycle

Main motivator for taking the pill: irritability, anger, uncomfortable feeling

Time of the day: 17:30 pm.

Dose: one dose of 12.5 mg plus one dose of 25 mg. (Total 37.5 mg.)

Physical reaction: No perceived physical reaction.

Psychological reaction: No perceived psychological effect.

Side effects: None.

Trial IV

Day of the menstrual period: Third day of her menstrual cycle

Main motivator to take 3-MMC: irritability (mood swings, emotional distress, impatience)

Time of the day: 19:30 pm.

Dose: one dose of 25 mg plus one dose of 12.5 mg. (total 37.5 mg)

Physical reaction: By one hour after administration Katy began feeling a slight increase in heartbeat and began to sweat. The sweating lasted two more hours. Three hours after administration she had lost her appetite, the feeling persisting until six hours after administration.

Psychological reaction: After one hour Katy felt very much calmer and much more relaxed than usual. She was not significantly upset, no longer irritable and felt energetic and willing to undertake tasks.

Side effects: Sweating and appetite loss.

Trial V

Day of the menstrual period: Five days before of her menstrual cycle (Second month of the trial)

Main motivator for taking the pill: irritability and anger (emotional distress)

Time of the day: 15:30 pm.

Dose: two doses of 25 mg. (one hour interval). Total: 50 mg.

Physical reaction: Slight increase in heartbeat after first dose and elevated heartbeat after the second one. Sweating after three hours no appetite.

Psychological reaction: "In a flow" state of mind, concentrated, very sharp and energetic, no longer angry although she could still feel irritated. This energy lasted for the rest of the day.

Side effects: Increased heartbeat, sweating and loss of appetite.

Trial VI

Day of the menstrual period: Four days before her menstrual cycle

Main motivator for taking the pill: irritability and anger

Time of the day: 11:30 am.

Dose: Two doses of 25 mg (total 50 mg within one hour)

Physical reaction: No physical reaction following the first dose, after the second dose a slight increase in the heartbeat and sweating for a few hours. Four hours after administration Katy noticed a loss of appetite.

Psychological reaction: Following the second dose Katy felt energetic, enthusiastic, extrovert, talkative but still upset. After three hours she was still hyperactive and only after four hours she calmed down. She experienced reduced irritability and anger, but afterwards experienced a sense of depression or being "down" for an hour. After that, and for the rest of the day, she felt "OK".

Side effects: Increased heartbeat, sweating, loss of appetite and a brief sense of feeling "down".

Trial VII

Day of the menstrual period: Two days before her menstrual cycle

Main motivator for taking the pill: irritability, anger and impatience

Time of the day: 17:30 pm.

Dose: Two doses of 25 mg with an interval of one hour. (Total 50 mg)

Physical reaction: No noticeable physical reactions.

Psychological reaction: After the second dose, Katy felt more energetic, less irritated and after two hours she was very calm. Her anger and impatience declined also after the second dose. However, one hour later she felt irritated again and four hours after that Katy felt more stable again.

Side effects: No noticeable side effects.

Response: Since Katy had acknowledged and was convinced from the beginning of not being sensitive to the effects of medication, she chose to start with a dose of 37.5 mg. She tried this dose four times, administered at least for two consecutive days around her period. The main physical reactions were increased heartbeat, sweating (the first hours) and depressed appetite later on and for the rest of the day. Psychologically speaking she stated feeling "high", more aware of herself, more concentrated, energetic, daring, calmer, but she would still be irritated or angry. Since anger was the main sensation that she wanted to overcome she decided to increase the dose to 50 mg. in the last three trials. The main reason for this was that her perceived tolerance to the 3-MMC and that the physical symptoms (side effects) were decreasing or disappearing. With a dose of 50 mg. Katy felt again, at the beginning (for the first two times), increased heartbeat, sweating, hot and depression of appetite, but the third and last time, these physical reactions did not appear. On the emotional side, Katy realized she was calmer and that situations that could have irritated her before didn't provoke anger in her anymore, but the calmness was short-lived for her. She also noted having had a brief period (one hour) of depression, which disappeared when the effect of the 3-MMC was gone (note that Katy had been diagnosed with an episode of depression one year ago).

Example V—"Diana"

Diana is a 21 year old healthy female, (weight between 43-45 kg. and 1.60 meters tall), from Austria, who works part time and also studies at a local university. She lives alone and is in a relationship. Diana stopped using oral contraceptives, which she was using to regulate her mood swings, but now she wants to try 3-MMC. Diana has never been pregnant and her menstrual periods are regular.

Menstrual Cycle-Induced Symptoms

Diana participated in the trial due to psychological and emotional complaints in relation to her menstrual period. Her menstrual cycle-induced symptoms typically begin about 4 days before onset of menses but persist during menstruation. At the end of her menses she "starts to feel like herself again". Menstrual-cycle induced symptoms have been a part of her cycle ever since her menarche.

Typical symptoms:
(Chronic)
Mood swings
Feeling down
Anxiety
Irritability/being upset
Exhausted or tired
Over sensitive
Lethargy/tiredness
Alteration in Libido
Will to cry/cry for no reason
Occasional symptoms:
Feeling alone/helplessness
Depression
Powerlessness
Eating disorder/craving Diana has been experiencing all of these symptoms ever since her menarche.

Background

Diana is overall a healthy person, but her menstrual cycle-induced symptoms have been consistent since her first period. About four days before menstruating she starts to feel irritable and gets into fights with her partner/boyfriend. Her symptoms continue during the first days of her period, she still feels irritable and also tired. At the end of her period she feels normal again.

She tried to get more control of her symptoms using oral hormonal contraceptives, but these caused her migraines and therefore she started seeking other solutions. Before and during her menses she experiences annoying, inconvenient feelings and would like to be more in control of her menstrual cycle.

Diana's symptoms have a negative impact on her social life. They influence her romantic relationship because she feels more irritable and acts out, feels tired and has conflict with her partner. She would like to stay in bed all day but then pushes herself to go out and be social. She does not want her menstrual cycle-induced symptoms to interfere with her daily life and tries not to show anything towards others. The only people she discusses her symptoms with are the women in her class at university. She feels that her experience is not very different from that of other girls, so it should be easier and normal for every woman to go through this. However, she feels that going through all the symptoms is "a lot". Diana's experience can be different depending on the activities she does during those days-for example, when she is at home and has more time to relax she feels better because she can rest. On busier days the symptoms can be a problem, a burden. In order to get more control she has tried homeopathic drops to relieve her of the mental and physical difficulties. However, in her experience the homeopathic drops did not work. Therefore she was interested in participating in the trial.

Summary

Petite female with symptoms compatible with moderate to severe PMS. She has been suffering distress related to her menstruation since an early age and continuously in time. In general she is a healthy young person.

Trial Period with 3-MMC

Duration 60 days with one menstrual period

Number of Trials

Three

Trial I

Day of her menstrual period: Diana's period was late, however she did experience PMS symptoms on the 21th day of the trial.

Main motivator for taking the pill: feeling out of control, feeling exhausted.

Time of the day: In the evening around 19:00. Empty stomach. She was worried she could not sleep because of the capsule but she did not experience insomnia.

Dose: one dose of 25 mg.

Physical reaction: After half an hour felt a boost in energy and she was no longer exhausted. She had the feeling of an increased heart rate, she felt more awake, after one hour she still felt the same. After 1.5 hours she felt more energized and the effect of the capsule slowly started to wear off.

Psychological reaction: After half an hour she was more focused, having a heightened mood, she felt less helpless and more in control; from feeling down to feeling happy and energized again. She was more willing to do things, felt impulsive ("we should go out!"). After one hour and a half she started to feel calmer and stable, and continued to feel happy and calm.

Side effects: stomach ache (on an empty stomach) and a higher heart rate, she explains it felt like a "caffeine rush".

Symptoms that were specifically relieved: She felt less distracted than normal, experienced no emotional distress or feeling down or any tension. Normally during the days of her menstrual cycle she feels helpless, exhausted, cries for no reason and has a desire to be alone.

She did not experience any of those symptoms when using the capsule.

*Notes after First Trial:

"I was very satisfied with my first experience with the pill, there was an extreme shift in my mood and well-being, which I noticed only shortly after taking it. However, I think the smaller pill would have been sufficient, as the psychical effects were too intense. I can see myself taking lighter dosages in the future. I also had no difficulties falling asleep despite my boost of energy" (Diana).

Trial II

Day of her menstrual period: 1st day of her period (late menstruation)

Main motivator for taking the pill: Feeling exhausted and depressed, feeling down the whole day. She has zero energy on the first day of her period.

Time of the day: In the evening. She did not eat before taking the capsule.

Dose: 1 dose of 12.5 mg.

Physical reaction: Stomach ache, she took the pill on an empty stomach and experienced some stomach pain for the first 30 minutes. After one hour she felt more energized, but not as strong as the first intake of 25 mg. She felt her normal self again after 2 hours, but felt possibly more energized than normal. After 4 hours no more effects.

Psychological reaction: After half an hour she had a slightly heightened mood, she wasn't as happy as the first time, but wasn't feeling depressed as before. She experienced a more stable mood and was able to start with her homework. After one hour and a half hour she felt less focused but was still feeling more emotionally stable. After two hours she felt more awake than before she took the pill. After three hours she was feeling down again but still less lethargic than before. After four hours the effects of the capsule had worn off.

Side effects: Stomach pain.

Definitely the participant felt less depressed, not lethargic, down or exhausted anymore.

*Notes after second intake: "The effects of the lower dose were significantly milder; I had the feeling that after two hours the effects of the pill had almost completely worn off. That day I had gone earlier home due to my menstrual symptoms. After I took the pill I felt like I would have possibly been able to continue working if it hadn't been for my cramps (which the pill had no effect on)" (Diana).

Trial III

Day of her menstrual period: Second day of her period.

Main motivator for taking the pill: same as the day before, feeling down and exhausted.

Time of the day: early afternoon, she ate something before taking the pill.

Dose: 1 dose of 12.5 mg.

Physical reaction: feeling more awake and more alert. After 3 hours she felt normal again, like she was not having her period, she felt like herself again.

Psychological reaction: She was no longer feeling down and exhausted. The participant was feeling more productive, more in control and optimistic, no sudden happiness as the first time (like it happened with a 25 mg. dose). After one hour she felt more focused, productive and stable. After three hours she slightly started to feel tired again.

Side effects: none.

Symptoms that were specifically relieved: Exhaustion, feeling down, mood swings, feeling alone and helpless, over sensitive, powerlessness, forgetfulness, willing to cry, feeling more focused, feeling out of control.

*Notes after Third Intake:

"I have the feeling that taking the pill two consecutive days made the effect of the second one last longer. 24 hours after I took it I felt much more calm and comfortable than I usually would in the middle of my period, even though I didn't take an extra additional pill" (Diana).

Results:

This participant was quite skeptical before the start of the trial. She thought she was in a placebo group and was not expecting to have any effect from the capsules whatsoever. She hoped that it would help her to get on top of things, get more control. Diana was pleasantly surprised with the effect the pills had on her. She tried different doses in three trials, the first time 25 mg and the two times after that 12.5 mg. She used one pill the first time, around the days she normally experiences menstrual cycle-induced symptoms, however her period was late. The second and third intake took place during the first days of her (late) period. The main side effects were increased heartbeat and stomach pain on empty stomach. Psychologically speaking she acknowledged feeling more focused and energized, a boost in her mood that made her be more impulsive. She did experience a higher heart rate. After this she wanted to try the lower dose to see if it would have a less dramatic effect. With a lower dose of 12.5 mg she felt energized and less lethargic or tired, her heartbeat seemed normal. On the emotional side, she was more focused, calmer, more controlled and with a more stable mood.

Example VI—Emma

Emma is a 23 year old female, originally from India, raised in Saudi Arabia, (60 kilos, 1.68 m.) average height and weight, full-time student, highly educated. She lives alone, and is in a relationship. She doesn't use any form of contraception. Her periods are regular and she has several psychological symptoms associated to her menstrual cycle. These symptoms have been worsening in the last years.

Menstrual Cycle Induced-Symptoms Emma participated in the trial due to the emotional distress she associates with her period, being some of the disturbing symptoms already present since an early age.

Usual acknowledged, chronic menstrual cycle-induced symptoms: (always or almost always)
  Emotional distress (since her menarche, 12 years old)
  Mood swings (since she was 12)
  Eating disorder/craving (since she was 12)
  Willing to cry for no reason (at least for one year)
  Feeling down (at least for the last five years)
  Feeling alone/helpless (at least for one year)
  Depression (past two months)
  Less frequent symptoms (sometimes) but present through time:
  Irritability/upset (since she was 12)
  Restlessness/nervousness (for five years)
  Anxiety (for the last five years)
  Desire to be alone (for the last five years)
  Burst of energy (for the last five years)
  Feeling out of control (past two months)

Background

Emma's reaction and attitude towards her symptoms has changed overtime. When she was a young girl, she was more introvert and reserved. As she got older this changed and she could notice how emotional she becomes around the time of her period. A week prior she already starts to notice changes that get worse a couple of days before menstruation.

Irritability is the most common symptom. A week before her menstruation she feels uneasy and questioning herself all the time, but then, everything goes back to "normal" after her period is over. She has regular periods, but they usually last for 7 to 10 days. If her periods are too late or too soon, she associates this phenomenon to her stress levels. She is very aware of her periods and keeps a good track of them.

The unrest before her period is felt not only by herself, but sometimes also people around her notice changes in her personality. She discusses these problems with close people, basically with everyone except for her father. Interesting to mention that her sisters experience the same type of symptoms around their period, they get upset and angry as well.

On one hand Emma considers that her personality changes are a normal part of the menstrual cycle, but on the other hand she would like to see it differently, during her menses she's more "in a shell" although she is actually a very social and outgoing person. Sometimes she forces herself to be with her friends and do things she likes during those days.

Since she also suffers from physical pain and cramps, she has been trying different strategies to cope with them, like comfort food (chocolate) and painkillers. She loves coffee but her cramps get worse with coffee. She has also tried physical exercise; walking, running, going to the gym helps her to forget the discomfort.

Summary

Emma is a healthy 23 year old woman who suffers from moderate to severe menstrual cycle-induced symptoms perhaps PMS, some of them since her menarche. She is very aware of the influence of her menstrual cycle on her personality so she is very open to talk about it and tries to have a positive attitude. PMS symptoms seem to run in all female members in the family.

Trial Period with 3-MMC

Duration 60 days with three menstrual periods in between—(second semester 2018)

Number of Trials

Seven

Trial I

Day of the menstrual period: 5th day of her menstrual period

Main motivator for taking the pill: Feeling low, wanting to cry for no reason, anxiety Time of the day: 15:00 μm in the afternoon.

Dose: one dose of 12.5 mg.

Physical reaction: The body felt warmer, a bit hot-this reaction took place very fast, after half an hour.

Psychological reaction: Emma felt calmer, less anxious and more in control of her actions; she was no longer feeling down, this sensation started after one hour and it had its peak after 4 hours and started to fade away in 6 hours.

Side effects: none (apart from feeling warmer).

Trial II

Day of the menstrual period: 6th day of her period

Main motivator for taking the pill: anxiety and nervousness

Time of the day: pill at 13:00 pm. After lunch

Dose: one dose of 12.5 mg

Physical reaction: feeling warm and comfortable, this time the reaction was slower, she started to feel changes after two hours.

Psychological reaction: Experiencing less anxiety and nervousness, feeling calmer, this reaction took place after one hour but it was weakly perceived.

Side effects: none

Trial III

Day of the menstrual period: A week before her menstrual period, PMS

Main motivator for trying the pill: Feeling low, sad, anxious, very distressed. This time she decided to take a higher dose to get stronger desired effects.

Time of the day: intake at 15:00 pm.

Dose: one dose of 25 mg.

Physical reaction: Feeling warmer, (perceived increased body temperature) after half an hour of pill intake and would last a couple of hours.

Psychological reaction: Emma was no longer feeling low, anxious or distressed. She would call it a "Zen moment", quieter, calmer, these changes started to take place a half an hour after administration of the pill.

Side effects: none

Trial IV

Day of the menstrual period: 5th day of the period

Main motivator for taking 3-MMC: Emma wanted to experiment with the pill on a more "normal" day because she was not feeling particularly distressed but was curious about the possible effects of the pill in that situation.

Time of the day: pill at 13:00 pm. Without having had lunch yet.

Dose: one dose of 25 mg

Physical reaction: feeling hot (warmer) after one hour and very hungry after two hours.

Psychological reaction: feeling focused and motivated to study; this reaction had its peak after two hours and lasted for two hours more.

Side effects: None

Trial V

Day of the menstrual period: 10th day of her period

Main motivator for taking the pill: She wanted to be more in control, concentrated and motivated to study Time of the day: pill at 13:00 pm. Without lunch Dose: one dose of 25 mg Physical reaction: feeling hot and hungry after two hours, she ate enough but she felt hungry again after one hour.

Psychological reaction: feeling focused and more concentrated, able to read and study with a lot of energy for about four hours.

Side effects: none

Trial VI

Day of the menstrual period: 11th day of her period

Main motivator for taking the pill: She needed to study like the day before (second day in a row)

Time of the day: pill at 13:00 pm. without lunch Dose: one dose of 12.5 mg

Physical reaction: less hungry (maybe accumulative effect—she had taken a pill one day before), feeling a bit warm, not as much as in previous occasions.

Psychological reaction: not very focused, only a little, (this on a small dose).

Side effects: none

Trial VII

Day of the menstrual period: one week before predicted date of menses

Main motivator for taking the pill: Emma reports being a bit emotional and in need to study and be focused Time of the day: pill at 16:00 pm. With food Dose: one dose of 25 mg Physical reaction: After one hour she really started to feel cold (body, hands and feet mainly) and hungry, although she had eaten before pill intake Psychological reaction: Emma achieved what she wanted; she could focus and concentrate on her studies and was also more motivated. This positive effect had its peak in two hours, lasted for two more and slowly after six hours faded away.

Side effects: Cold hands and feet

Results:

Emma began with a dose of 12.5 mg that already produced a positive effect in terms of calming her down and relaxation. This effect increased with a higher dose of 25 mg., with Emma also perceiving being more focused, able to concentrate and more motivated to do things. Her first three trials were related to menstrual cycle-induced distress, however later on she said she wanted to try taking the pill during periods when she was not particularly anxious, but when she needed to study. According to her she was very pleased with the discovery that the pill helped her to concentrate on her readings, be more focused and motivated to study. Thus, in the last four trials she took one small dose and three high doses with a marked effect on her concentration levels with a higher dose. With all doses (low or high) and in all trials Emma noticed body temperature changes. She almost always felt warmer; however this was not uncomfortable for her. Only once, Emma felt suddenly colder, especially hands and feet. It is probable that she could have had changes in her appetite due to pill but she is not sure about it. The pill had an effect, on average, after one hour, would last for a couple of hours and then completely dissipate after six hours.

Example VII—"Fanny"

Fanny is a 21 year old female student from Finland, in a relationship and living with her boyfriend (height 1.60 meters, weigh: approx 50 kilos). She is a healthy person, and uses intrauterine contraceptive device. She has regular menstrual periods which are always accompanied by uncomfortable menstrual cycle induced symptoms.

Menstrual Cycle-Induced Symptoms

Fanny participated in the trial due to her mainly emotional complaints in relation to her menstrual period. Her symptoms usually begin a week before but the distress around her period can be also present for the duration of her menses, which has lately become longer.

Typical menstrual cycle-induced symptoms (chronic):

Feeling down (for years, she would not state for how many)

Mood swings (for years)

Exhausted and tired (for years)

Over sensitive (for years)

Willing to cry for no reason (for years)

Less frequently observed symptoms (occasionally):

Forgetfulness (for the last years)

Irritability/being upset (for the last months)

Restlessness or nervous (for the last months)

Impatient (for the months)

Lethargy (for the last months)

Concentration difficulties (for the last months)

Acting out (for the last months)

Background

In the days around onset of menses, Fanny often feels down, moody, exhausted, over sensitive, willing to cry. She has been having most of these symptoms for years already. In the last year the symptoms have become worse, and sometimes Fanny feels nervous, restless, upset, impatient, forgetful, tired, and distracted. All these emotions and states are felt usually a week before her period and even some days after it. In the last years the duration of her menses has become longer than before, up to seven days.

Even though Fanny has been distressed by menstrual cycle-induced symptoms for years; her symptoms worsened after finishing school and starting university. She states that her symptoms have no relation to the contraceptive method she chooses, because they started much before she decided to use an IU device.

In general, she hardly has physical (somatic) issues related to her period, most of the time only a slight pain that goes away with an over the counter painkiller.

She has an open and direct attitude towards menstruation. She had her menarche when she was 12 years old and she took it in a very natural way. Her mother also has severe symptoms related to her menstruation as well as her older sister "it runs in the family" as she puts it. For sure during those days her relationship with her boyfriend and friends may be affected, but she is not the indoors type and opts to carry on with her life. When things get really worse, horse-riding is always a good medicine for Fanny.

Summary

Fanny is a healthy 21 year old young woman who suffers from moderate to severe symptoms associated to PMS. Other female members in the family also present strong PMS symptoms. Her emotional distress has been consistent over time since her menarche.

Trial Period With 3-MMC

Duration 60 days with two menstrual periods in-between—(second semester 2018)

Number of Trials

Five

Trial I

Day of the menstrual period: 20th day period, 9 days before period

Main motivator for trying 3-MMC: Irritability and inability to focus

Time of the day: 11:30 am after breakfast

Dose: one pill of 12.5 mg.

Physical reaction: Fanny experienced muscle relaxation after half an hour, after one hour tingling in the muscles and tingling at the back of the tongue/throat. These sensations continued up to two hours. She also reports feeling sleepy but after two hours the sleepiness was gone.

Psychological reaction: Still irritable until first hour after intake but then later her mood got better, less irritable but not a major difference. Next day she felt upset again.

Side effects: Tingling tongue, light somnolence

Trial II

Day of the menstrual period: 24th day period, four days before her period (PMS)

Main motivator for trying 3-MMC: General annoyance and irritation.

Time of the day: 10:50 am. After breakfast

Dose: 25 mg.

Physical reaction: After half an hour, relaxation and drowsiness, a bit tired or sleepy, increased muscle pain, more tension in some specific muscles around the shoulder, after one hour the muscle pain was gone. Some stomach pain for some minutes (after one hour). Tingling in the throat, which remained for around two hours.

Psychological reaction: Fanny felt a change, she felt relaxed, calmer. An hour after administration she felt happier and able to concentrate (up to four hours); feeling good for the rest of the day and not irritable or annoyed any more. The following days she felt very good.

Side effects: drowsiness and some muscle pain or tension

Trial III

Day of the menstrual period: 27th of the period, one day before her period (PMS)

Main motivator for trying 3-MMC: stress and irritation, (very busy time at the faculty)

Time of the day: 10:35 am after breakfast

Dose: one dose of 25 mg.

Physical reaction: After half an hour muscles relaxed, slight stomach pain (it could have been related to the period), no change in appetite. After one and half hour some reported tension in the shoulder muscles, increased energy. Two hours later Fanny felt sleepy and still experienced muscle tension. Sleepiness as well as muscle tension abated after three hours. 24 hours after administration, Fanny was still feeling good.

Psychological reaction: One half hour following administration, Fanny felt calmer and stable, after one hour able to concentrate well, after one hour and a half she was fully concentrated and glad to study, not feeling stressed, irritated or worried anymore, the rest of the day was fine.

Side effects: Not willing to go to the gym, physically not fit for the challenge. Temporal slight stomach and muscle pain.

Trial IV

Day of the menstrual period: 3rd day of the period

Main motivator for trying 3-MMC: extreme annoyance and anxiety (upsetting news)

Time of the day: 13:45 am after lunch

Dose: one dose 25 mg.

Physical reaction: After half an hour, no changes, after one hour numbness and relaxation, after one hour and a half goose bumps and feeling cold, temperature changes. After two hours the cold feeling disappeared but muscle tension and tingling remained.

Psychological reaction: After half hour calmer and remained like that despite some very upsetting news, Fanny recognized herself to be very worried, but with no physical reaction, and her body felt "under control". She was upset but accepting the situation, it was easier to deal with. After two hours feeling well, Fanny decided to stop procrastinating and study. She was not concentrating very well but no longer feeling upset, felt a lot calmer. Six hours later she was still focused, feeling "calm and collected".

Side effects: Perceived body temperature changes, tingling sensation in the throat.

Trial V

Day of the menstrual period: Three or four days before her period (PMS)

Main motivator: Irritability, willing to cry, not feeling emotionally good

Time of the day: 21:50 pm after dinner

Dose: one dose 25 mg.

Physical reaction: No reaction perceived after one hour, later an increased sensitivity in the scalp, tingling at the back of the throat, hands and feet were colder around 11 pm. After 1½ hour experienced stomach pain and more sensitivity, after two hours Fanny felt well again, but had difficulty falling asleep. It took Fanny an hour to fall asleep. After 24 hours she felt "normal" again.

Psychological reaction: After half an hour Fanny did not feel very emotional, after one hour she was still upset but not willing to cry anymore, after one hour and half feeling emotional again. Small, but transient improvement in her mood.

Side effects: Difficulty to go to sleep.

Response:

The subject took the pill on five occasions, three of them some days before her period and two of them during her period. During all trials Fanny was suffering from emotional distress. The first time she took a dose of 12.5 mg. and the four other times the dose was 25 mg.

A pill of 12.5 mg had a mild effect on Fanny but she could already experience a state of being calmer and more relaxed emotionally speaking. On all other occasions, when she took a dose of 25 mg. she felt significant calmer, under control, more focused and collected. She felt could be more proactive and energetic at a mental level. On one occasion she took the pill because she was much distressed by unfortunate family news and feeling completely out of control. Fanny noticed how the pill kept her reactions under control: she was still very much worried about the situation, but instead of crying she could still sit down and work. This produced a good feeling afterwards.

The physical reactions could be considered "mild" side effects and some of them were present in all trials even with the small dose: an unfamiliar tingling at the back of the tongue and throat for around two hours after administration. Fanny experienced a general sense of relaxation, but also some specific muscle tension in the area of the shoulders and sometimes a very brief stomach pain (five to ten minutes). Fanny reported feeling too sleepy or numb to undertake physical activities but very much alert for undertaking mental ones. On one occasion, Fanny experienced body temperature changes, cold hands and feet, and goosebumps. When she took the pill at night, she had difficulty time falling asleep in spite of feeling calm.

Example VIII—"Ines"

Ines is a 19 year old student from Hungary living in The Netherlands, (1.62 m. tall and 47 kilos). She is not in a relationship and she does not use any form of contraception. She lives alone and shares a house only with the landlord. Her menstrual periods are regular and with no problems other than emotional distress.

Menstrual Cycle-Induced Symptoms

Some days before her period Ines, starts feeling uneasy, although her symptoms are not severe enough to interfere with her daily life, but they are strong enough to remind her that soon she will be menstruating.

Acknowledged menstrual cycle-induced symptoms, chronic:

Hypersensitivity (since her first period)
Emotional distress (always)
Mood swings (always)
Indecision (last few years)
Occasional menstrual cycle-induced symptoms:
Exhaustion, fatigue (recent few years)
Powerlessness (recent few years)
Lethargy/tired (recent few years)
Will to cry/crying jags (since menarche)
Background A few days before her period Ines usually feels emotionally distressed and very tired. She has no sisters to compare her symptoms to, but her mother never complained about difficult days around her menstruation. Thus Ines says that: "the issue may not run in the family". When she feels uneasy due to her approaching period, she usually decides to nap and take it easy. Ines tends not to exercise or exert herself, as the PMS affects her mood and personal drive.

Her menarche took place when she was 12, with a natural, uncomplicated course, no stress at all; but with the years Ines noticed increasing over-sensitivity and emotionality. The psychological distress she experiences is usually the reminder that her period is about to begin. She has regular periods of 28 days and they usually last around 5 days. Ines was never formally diagnosed with PMS. She associates the worsening of her symptoms to changes in her life, passing from school to university, for example. Ines has what she considers to be a normal social life, and there are no problems with her relationships and social interaction even while experiencing menstrual cycle-induced symptoms. Ines discusses her menstruation very openly.

Summary

Ines is a healthy 19 year old young woman who suffers from moderate menstrual cycle-induced symptom. There are no records that other female members in her family are affected by this. Her emotional distress has been getting progressively worse over the time.

Trial Period with 3-MMC
Duration 60 days with two menstrual periods in between—(second semester 2018)

Number of Trials
Seven
Trial I

Day of the menstrual period: day 27th of her period, 1 day before period

Main motivator for taking the pill: Emotional distress and curiosity about what the pill could do for her.

Time of the day: 17:00 in the afternoon
Dose: one dose of 12.5 mg.
Physical reaction: None perceived.
Psychological reaction: Feeling more at ease after one hour, more relaxed, less emotionally distressed. The feeling lasted up to three hours.
Side effects: None Trial II Day of the menstrual period: First day of the period
Main motivator for taking the pill: A bit of tension
Time of the day: 18:00 in the evening
Dose: 25 mg.
Physical reaction: None perceived.
Psychological reaction: After the first half an hour from administration Ines already felt more relaxed, less tense and after a couple of hours more energetic, then after four hours back to normal, the way she feels on any day but calmer.
Side effects: None and no relation with her sleeping hour that night.

Trial III

Day of the menstrual period: 2nd day of her period
Main motivator for taking the pill: feeling a bit tense and with headache
Time of the day: 10:00 am after breakfast (less than 24 hrs. after last pill)
Dose: one dose 12.5 mg.
Physical reaction: After one hour the headache abated.
Psychological reaction: Calmer and more stable half an hour after administration, after one hour feeling more content and relaxed. More motivated to undertake mental than physical tasks.
Side effects: None Trial IV Day of the menstrual period: 26th day of the period, two days before period
Main motivator for trying 3-MMC: feeling "down" and upset, lack of motivation
Time of the day: 10:00 in the morning after breakfast
Dose: one dose, 25 mg.
Physical reaction: None
Psychological reaction: Little reaction one half hour after administration, after one hour feeling noticeably less upset and less sad, with that feeling remaining throughout the remainder of the day. Also more energetic. The effects of the 3-MMC lasted up to six hours
Side effects: None Trial V Day of the menstrual period: Day 27th of the period, one day before menstruation
Main motivator for taking the pill: Emotional distress
Time of the day: 10:00 am after breakfast
Dose: one dose of 12.5 mg.
Physical reaction: None.
Psychological reaction: One half an hour following administration: less mood swings, less upset, less emotional and less tired. (Could be a accumulative effect-Ines was taking them consistently for some days before her period).
Side effects: None Trial VI Day of the menstrual period: First day of menstruation
Main motivator for taking the pill: Emotional distress and nervousness.
Time of the day: 11:00 am after breakfast
Dose: one dose 12.5 mg.
Physical reaction: None, perhaps reduced tension
Psychological reaction: Ines felt calmer, less nervous and emotional after intake but when the effects of the pill abated, tension returned, but milder.
Side effects: None Trial VII Day of the menstrual period: 2nd day of menstruation
Main motivator for taking the pill: Emotional distress, tension, sense of helplessness.
Time of the day: 10:00 am after breakfast
Dose: one dose 12.5 mg.
Physical reaction: None.

Psychological reaction: Ines felt better very quickly, less distressed and tense. She was calm and content, the pill seemed to have more of an effect than the days before, the tension faded away rapidly. Possibly a cumulative effect.

Side effects: None

Response:

The subject used the pill on seven occasions (alternating doses of 12.5 mg and 25 mg.) and during all of them she maintained a normal hectic university-student's life, so that her "life rhythm" was not altered by any disruptive event. However, still during menstrual cycle-induced symptoms Ines was feeling emotionally distressed, which is why she used the pill:

three in a row, before every period. She experienced no side effects or physical reactions worth mentioning. The main effect was calming and relaxing, not really focused (as other participants have mentioned). Although her peers might not have noticed any change in her, Ines felt more prone to accept the people around her. Although no significant dose response has been observed, it is possible that there was a sort of a cumulative positive effect following administration of the pill in less than 24 hrs. (This needs to be corroborated by further studies). However, one must note that Ines herself also acknowledged that the duration of the effect of the pill was no more than four to six hours.

Example IX—"Jenny"

Jenny is 24 year old female of mixed origin (German and Turkish). She is 170 m. tall and weighs 65 Kg. She participated in the study because she suffers from moderate to severe menstrual cycle-induced symptoms some days before her period. She studies and works in The Netherlands. She lives with flat mates and she has a long-distance relationship with her boyfriend. She doesn't use any form of contraception and she has regular periods of around 24 days which last from 3 to 4 days.

Menstrual Cycle-Induced Symptoms

Jenny suffers from some distinctive chronic menstrual cycle-induced symptoms (for a few years at least):

Frequent symptoms:

Emotional distress (some years now)

Feeling "down"

Eating disorder: craving

She also experiences occasional:

Exhaustion or fatigue (a couple of years)

Depression

Feeling alone or helplessness

Desire to be alone

Desire to be silent

Will to cry with no reason/Crying jags (some months)

Background

Jenny experiences severe symptoms 4 to 5 days before her period. She has emotional issues which are also related to body pain and digestive problems. Her symptoms have been getting more aggravated over the years. Most of the time Jenny realizes that she is going through physical and psychological distress, and other changes around the time of her period and this, in turn raises her consciousness about the symptoms, and helps her monitor her menstrual cycle. She doesn't take any special measure to overcome her problems but she usually goes running to relax, something that she would like to do during her period, but, paradoxically she doesn't feel like exercising on those days.

When the menses subside, Jenny feels like going back to normal again, and feels sort of relieved from the emotional burden and "happy" again; and this flow of feelings comes regularly every month.

Her menarche was a natural process; all in all it is recalled as a positive experience and she remembers being excited about it. She also remembers going through a period of time when her menstruation had stopped or was irregular and she did not feel good about it. Jenny does not like the days prior to the onset of menstruation, but she also feels it is a process that she needs experience in a natural and healthy way.

Jenny acknowledges that her social and work relationships may be affected by her menstrual cycle-induced symptoms. She talks openly about this to close relatives and has discussed it with her mother and sister who also seem to experience the same menstrual cycle-induced symptoms.

Summary

Jenny is a healthy 24 year old young woman who suffers from moderate to severe menstrual cycle-induced symptoms. Some of these symptoms started a few years ago, but they have been progressively worsening in the last few months. Her mother and sister also suffer from emotional distress around their menstrual period.

Trial Period With 3-MMC

Duration 60 days with two menstrual periods in between—(December 2018/January 2019)

Number of Trials

Four

Trial I

Day of the menstrual period: 21st day of her period, 4 days before menstruation PMS Main motivator for taking the pill: Unhappy, confused and emotionally distressed.

Time of the day: 8:30 am in the morning after breakfast

Dose: one dose of 25 mg.

Physical reaction: None

Psychological reaction: After half an hour Jenny felt better, less anxious, less unhappy, feeling "normal" again (like when she is not experiencing menstrual cycle-induced symptoms), the good feeling kept up for a couple of hours and faded away without consequences.

Side effects: None

Trial II

Day of the menstrual period: 4th day of the period, last day of menstruation

Main motivator for taking the pill: Jenny was totally exhausted, headachy, lacking energy and feeling down.

Time of the day: 17:00 μm.

Dose: Two doses of 12.5 mg, equivalent to 25 mg.

Physical reaction: The headache remained in the background and after the effect of the 3-MMC faded away Jenny could still feel physical fatigue Psychological reaction: After half an hour she started to feel better, after an hour Jenny felt more energized, no longer down or sad and this positive effect lasted around two hours.

Side effects: None.

Trial III

Day of the menstrual period: 12th day of her period (possible ovulation)

Main motivator for trying 3-MMC: exhausted, powerless and tired, willing to cry

Time of the day: 18:00 pm after work

Dose: one dose of 25 mg.

Physical reaction: An underlying physical tiredness remained

Psychological reaction: Half an hour after administration Jenny felt better and more relaxed, after one hour and half she felt very good and motivated to do things. The feeling of powerlessness was gone and no will to cry anymore.

Side effects: None

Trial IV

Day of the menstrual period: 21th day of the cycle, 7 days before period

Main motivator for taking the pill: Extreme sadness with no reason, lack of motivation and energy, strong will to isolate, lack of appetite, headache.

Time of the day: 10:00 am after breakfast Dose: one dose of 25 mg.

Physical reaction: Jenny's appetite returned within one hour after administration, when she started to feel psychologically better. At the end of the day, she no longer felt sadness or headachy.

Psychological reaction: One half hour after administration Jenny started to have a bit more of energy and not feel down anymore. Her sadness faded away. After one hour she started to have more energy, was able to get some work done and to socialize (no longer the desire to be alone). After one hour and a half she was at the top of good predisposition and performance.

Side effects: None

Response:

The subject took the pill on four occasions, in all four the dose was the same: 25 mg. She had a positive experience during all trials. In all four trials she conducted a normal life of work and study, without particularly distressing situations, but on the last occasion, she was particularly gloomy, sad and willing to isolate. In general, the experience was surprisingly good for her, somehow she felt better even though she thought at first that the beginning that taking the pill would not be effective. She stated that there was a clear difference in her mood from before and the after pill. The effects did not last long in Jenny's case though, just a couple of hours; however, the crisis was gone and this helped her to feel well again or as she says "normal". For her being normal means not having weird thoughts and not being anxious. Overall the pill helped her to be more focused and positive towards her life, which was very comforting, especially because the good feeling would remain for the rest of the day.

Example X—"Rebecca"

Rebecca is a 21 year old healthy female, (50 Kg., and 1.60 m. tall), she is from the Netherlands, studies and works part time. She is in a relationship, she shares house with other people. She discontinued oral contraceptives because of the side effects and tried an intrauterine device. Right now she is not using any hormonal contraception. She has used the abortion pill once and her menstrual periods are regular, around 28 days.

Menstrual Cycle-Induced Symptoms

Rebecca participated in the trial due to psychological and emotional complaints in relation to her menstrual cycle. Her menstrual cycle-induced symptoms usually start about two days before her period but she can still feel the symptoms during her menstruation. These menstrual cycle-induced symptoms have been a part of her cycle for some months now.

Typical menstrual cycle-induced symptoms: (Chronic)

Emotional distress

Mood swings

Feeling down

Irritability/being upset

Restlessness/nervousness

Tension

Feeling alone and helplessness

Over sensitive

Confusion

Indecisiveness

Desire to be alone

Desire to be silent or to talk (she emphasis her desire to be silent)

Difficulty concentrating or distract

Changes in the libido

Decreased interested in usual activities

Others: feeling not mentally present/absence

Less frequent symptoms:

Depression

Anxiety

Exhausted or tired

Lethargic/tired

Acting out

Crying for no reason

Background

Rebecca is in general a healthy person, however when she was 15 she had an ovarian cyst removed. Her menstrual cycle-induced symptoms started more or less half a year ago; she experiences them severely some days before onset of menses. The symptoms can be physical symptoms (e.g. back pain), but also psychological/emotional symptoms like "feeling down" and aversion to social interaction. Social avoidance and lack of interest in social contact are the usual expressions of her emotional menstrual cycle-induced symptoms.

People around Rebecca notice her mood swings during her premenstrual and menstrual phase. These symptoms have an effect on her routine and on her work. Her boss sometimes notices she is not feeling well because she will only do things that are really necessary at work.

Her boyfriend knows she will have mood swings around her period and sometimes they have arguments about it, but they can also discuss her symptoms. Sometimes Rebecca thinks that what she experiences is actually worse than what people can perceive.

Years ago Rebecca tried the contraceptive pill, which left her depressed and experiencing less joy in her life. Later she tried an intra-uterine device but had it removed due to reduced libido. In order to gain more control over her symptoms, Rebecca has experimented with micro-doses of LSD that she eventually discontinued due to fear of addiction and undesired side effects.

Summary

Rebecca is a healthy, 21 year old female who suffers from moderate to severe menstrual cycle-induced symptoms (e.g. PMS).

Trial Period with 3-MMC

Duration 60 days with two menstrual periods in between (December 2018/January 2019)

Number of Trials

Three

Trial I

Day of the menstrual period: 3rd day of her period, during menstruation

Main motivator for taking the pill: Some previous days already feeling down, tired, easily irritated.

Time of the day: 13:00, after eating

Dose: one pill of 25 mg+one of 12.5 mg. (37.5 mg in total)

Physical reaction: After one hour her legs felt lighter, after three hours the sensation of tension around the head was relieved.

Psychological reaction: After one hour Rebecca felt more awake, more energetic, more alive, therefore less tired and irritated. She was more willing to do things. Negative feelings started to change in a positive way and, even if after the pills effect subsided, a positive sensation persisted.

Side effects: None

Trial II

Day of the menstrual period: 2nd day of menstruation

Main motivator for taking the pill: Mood swings, emotionally distressed.

Time of the day: 17:00 pm

Dose: 12.5 mg.

Physical reaction: None

Psychological reaction: None (she felt no effect whatsoever with this small dose).

Side effects: None

Trial III

Day of the menstrual period: 3rd day of the menstruation

Main motivator for taking the pill: Feeling really down and unhappy

Time of the day: 14:00 pm

Dose: one pill 25 mg.

Physical reaction: None

Psychological reaction: After one hour, less stressed and feeling "really easy going", her mood was "upgraded", relief of the sadness, not down or stressed anymore. This positive feeling lasted for three hours.

Side effects: None

Results:

Rebecca tried the pill in three different trials, first time a 37.5 mg dose, a second time 12.5 mg. and the last time 25 mg. As Rebecca suffers from her symptoms (e.g. distress, "down", social avoidance) not only the days before her period, but also during her period, she decided to try the pill during the first days of menses (her symptoms are more severe during those days). In the first trial, with the highest dose, Rebecca felt actually very good, so good that she recalls being a bit apprehensive because her gloomy feelings were replaced by uplifting and happy sensation. She felt somehow that this was not actually her; so the second time, she tried the smallest dose possible (12.5 mg), with no significant reaction, neither positive, nor negative. The third trial with 25 mg. produced a pleasant, positive change that subsided naturally keeping her in good mood. For Rebecca, 25 mg. seems to be ideal dose. She feels susceptible to addiction and she did not want to keep on trying with the pill out of fear that she would "like it too much".

Rebecca had no physical reactions or undesired side effects with any of the doses. She only remarked that falling asleep those days was not so easy (due to the late hour of the trials).

Example XI—"Pamela"

Pamela is a 20 year old female, 81 kg, 1.80 m. from Slovenia, she is a university student living with her boyfriend in the Netherlands. She does not use any kind of contraception method, and has never been pregnant. Her menstrual periods are often regular but are occasionally shorter or longer than 28 days. Her menstrual periods are in general very painful and she also has distressful emotional symptoms some days before.

Menstrual Cycle-Induced Symptoms

Chronic symptoms:

Decreased interest in daily activities (3 years)

Anxiety (2 years)

Craving for food (2 years)

Desire to be silent or talk (2 years)

Powerlessness (2 years)

Concentration difficulties (1½ years)

Frequent symptoms:

Moodiness (3 years)

Emotional distress (3 years)

Impatience (2 years)

Over sensitive (2 years)

Irritability (1 year)

Physical problems and pain (headache, bloated, breast tenderness, etc.) (5 years)

Occasional symptoms:

Feeling down (3 years)

Desire to be alone (3 years)

Forgetfulness (2 years)

Confusion (2 years)

Changes in the libido (2 years)

Nervousness (1 year)

Tiredness (1 year)

Background

Pamela is a healthy person, who in general avoids medication, except for during her period. She takes painkillers for the physical symptoms and homeopathic substances to keep her relaxed and under control (e.g. valerian leaves, that have a sedative effect).

She had her menarche when she was 14 years old. It was a normal and natural experience that became unpleasant in the last years due to stress and daily activities demanded by her studies. Pamela's symptoms worsened when she finished school. Her psychological state seems to affect her physiological activity, for instance, periods of stress can result in an alteration of Pamela's menses, to longer or more brief depending how worried or affected she is by an emotional stressor. Changes in her sleeping pattern can also affect the periodicity of her menstrual cycle.

She is very apathetic during her period and if she can choose, she prefers to stay at home and just rest and do nothing. Her boyfriend always notices a change in her behavior around her period, and they are conscious of how this can affect their relationship. There are no records that her sisters (2) or her mother may also suffer from menstrual cycle-induced symptoms. She speaks openly about this topic with her mother, family and people in general.

Summary

Pamela is a healthy young woman who has been suffering in the last two/three years from quiet stressing emotional symptoms associated with her menstrual cycle. She also suffers from physical pain. Pamela takes painkillers and sometimes also sedatives to cope with her symptoms, although she is not fond of medicines. She is mainly affected with moodiness, tiredness, pain, confusion, irritability, symptoms compatible with menstrual cycle-induced symptoms for their number and duration in time.

Trial Period with 3-MMC

Duration 60 days with three menstrual periods in between—(second semester 2018)

Number of Trials

Four

Trial I

Day of the menstrual period: 26th, three days before her next menstruation, experiencing symptoms.

Main motivator for taking the pill: stressed, anxious, not being able to concentrate or focus.

Time of the day: 12 am. After breakfast
Dose: one dose of 12.5 mg
Physical reaction: None
Psychological reaction: None.
Side effects: None
Trial II
Day of the menstrual period: 27th or two days before her period, experiencing symptoms.
Main motivator for taking the pill: Feeling overwhelmed, hopeless, distressed, stressed, a very difficult day
Time of the day: 13:00 am. After breakfast
Dose: one dose of 25 mg.
Physical reaction: No reaction
Psychological reaction: After one hour and half, experienced slightly less tension, and after two hours a bit more relaxed, less distressed-Pamela was no longer obsessed by her problems. Four hours after administration, she was more stable, but still feeling the pressure of a difficult day.
Side effects: None
Trial III
Day of the menstrual period: 2nd day, during her menstrual period.
Main motivator for taking the pill: Feeling bad, emotional distressed, powerless, low motivation, lack of energy.
Time of the day: 11:00 am after breakfast
Dose: one dose of 12.5 mg.
Physical reaction: None
Psychological reaction: None, not better nor worse
Side effects: None
Trial IV
Day of the menstrual period: 27th day of the cycle, two days before period, experiencing symptoms
Main motivator for taking the pill: emotional distress, crying with no reason.
Time of the day: 18:00 pm. After eating
Dose: one dose of 25 mg
Physical reaction: After one hour and half more cold than usual, then during a bath feeling very hot, fatigued after three hours, but unable to fall asleep after four hours.
Psychological reaction: After one hour and half a bit calmer, after two hours very relaxed, not crying anymore and then she felt a bit numb, later just stable but after six hours feeling low energy, without motivation again.
Side effects: somewhat tired and body temperature changes.
Results
Pamela took the pill on four occasions, two times a 12.5 mg. dose and two times a 25 mg. dose. The 12.5 mg dose did not have any effect, neither physical nor psychological. Effects of the 25 mg. dose were also not as relevant as with the other subjects: she felt a bit more relaxed and calmer but did not experience really positive effects. (Note-Pamela was the heaviest and tallest of all the subjects, and body mass may have influenced her response). Pamela also experienced some light and non-desirable effects such as body temperature changes.

Example XII. Overview of all Cases

Between the second half of 2018 and the first months of 2019, eleven women participated in a blinded trial of 3-MMC (the "pill") administered to alleviate their menstrual cycle-induced symptoms. The subjects tried different doses ranging from 12.5 mg. up to 50 mg.

Ten out of the eleven reported a rather good to a very positive experience, in other words: 3-MMC worked for the intended purpose, making them feel better and in some cases, much better.

It will be noted that while 3-MMC is not specifically targeted to alleviate physical distress or pain associated with menstrual cycles (e.g. headache, bloating, cramps) some of the common physical menstrual cycle-induced symptoms (e.g. headache) can be aggravated by tension or other results of emotional/psychological distress. Accordingly, in a number of participants in this trial administration of 3-MMC resulted in disappearance of somatic symptoms (e.g. headache).

One of the women in the research combined the 3-MMC treatment with paracetamol, without any noticeable substance interaction or undesired effect. Menstrual-cycle induced symptoms are commonly approached from the physical aspect. Combination of 3-MMC with the common remedies for somatic menstrual-cycle induced symptoms (e.g. painkillers) would likely broaden the spectrum of benefits of the treatment, for example, reduce the cause of work impairment for millions of women worldwide on monthly basis.

The women in the trial, except for "Gertie" (Example I), all reported moderate to severe menstrual cycle-induced symptoms (e.g. PMS). In some cases, due to the number of years suffering from distress, the severity and the amount of symptoms the clinical picture could be interpreted as dysphoria (PMDS) according to the DSM-5 manual.

Each one of the women used the 3-MMC for relief for at least two to three consecutive menstrual periods, with the number of trials varying from two to seven per woman, making a total of 45 trials. One of the subjects ("Gertie") has been experimenting with 3-MMC for menstrual cycle-induced symptoms (e.g. PMS), and has to date administered 3-MMC for her last fifteen menses ("Gertie" reports a radical positive life change).

Thus, the experience with 3-MMC for menstrual cycle-induced symptoms reported here is from approximately 60 separate trials.

FIG. 3 provides a summary of the indications for treatment by administration of 3-MMC according to the invention—i.e. the most typical complaints women would mention before the trial.

Results

Note—

This study endeavored to provide case studies, and, being qualitative in character, no statistics were employed in presenting these data.

Emotional distress in the form of uneasiness, irritability and tiredness are at the top of the list of the motivators for administering 3-MMC (see FIG. 1). According to the case studies the following effects were observed:

A desired positive effect was achieved with most trials. Low dose (12.5 mg) of 3-MMC, while not consistent, was often effective in providing relief of symptoms. In a few instances, high doses (35-50 mg) of 3-MMC were accompanied with undesirable side effects. In general, a dose of between 20 and 25 mg. 3-MMC proved effective, without significant reported side effects. At 30-35 mg. some undesired side effects, such as tachycardia or temperature changes were occasionally more noticeable.

Most commonly reported psychological and emotional effects of 3-MMC included: a sense of relaxation and calm, often combined with heightened energy and ability to concentrate, with a typical onset between half an hour and an hour after administration, lasting up to four hours, dissipating after six hours, and with a persistent sense of calmness following. The words used to describe the positive effects of 3-MMC can be seen in order of frequency in FIG. 2.

From some of the women's accounts it can be inferred that occasionally the feeling of being calmer can also produce a reduction in somatic symptoms (e.g. physical pain).

The responses indicate that 3-MMC can have a "cumulative positive effect"; after two or more consecutive trials (a second dose within 24 hours of the first dose and then a third dose within 24 hours of the second), it seems that 3-MMC's positive effects persist. Moreover, it seems that repeat administration allows for dose reduction of the consecutive doses with good results (e.g. an initial dose of 25 mg. followed by 12.5 mg. for two days seemed to offer more permanent relief). A similar phenomenon was observed with the undesired effects; side-effects tend to diminish over time with repeated use of 3-MMC.

The most commonly reported side effects include: tachycardia, sensation of body temperature changes (usually feeling warmer or sometimes colder) and sweating. There are also possible changes in appetite (loss of appetite could be a cumulative effect after several consecutive doses) or sleep pattern. Some of the subjects reported improved sleep while others reported difficulty trying to sleep. Some instances of brief periods of stomach pain on empty stomach and possible changes on the skin condition (rashes and pimples) were also reported (see FIG. 3).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of treating at least one menstrual-cycle-induced symptom in a subject in need thereof, the method comprising:
   determining a time at which said at least one menstrual-cycle-induced symptom is expected to occur, or has occurred; and administering a therapeutically effective amount of 3-methylmethcathinone (3-MMC), so as to treat the menstrual-cycle-induced symptom, wherein said menstrual-cycle-induced symptom is a symptom of a menstrual-cycle induced condition selected from the group consisting of perimenstrual disorder, Premenstrual Syndrome (PMS) and Premenstrual Dysphoric Disorder (PMDD).

2. The method of claim 1, wherein said at least one menstrual-cycle-induced symptom is expected to occur, or has occurred between 1-15 days prior to onset of menses.

3. The method of claim 2, wherein said at least one menstrual-cycle-induced symptom is expected to occur, or has occurred between 1-7 days prior to onset of menses.

4. The method of claim 1, wherein said at least one menstrual-cycle-induced symptom is expected to occur, or has occurred between 1-10 days following onset of menses.

5. The method of claim 4, wherein said at least one menstrual-cycle-induced symptom is expected to occur, or has occurred between 1-7 days following onset of menses.

6. The method of claim 1, wherein said at least one menstrual-cycle-induced symptom is expected to occur, or has occurred between 1-7 days prior to and between 1-7 days following onset of menses.

7. The method of claim 1, wherein said administering occurs prior to the time at which the menstrual-cycle-induced symptom is expected to occur.

8. The method of claim 7, wherein said administering occurs 1-5 days prior to the time at which the menstrual-cycle-induced symptom is expected to occur.

9. The method of claim 8, wherein said administering occurs 1-3 days prior to the time at which the menstrual-cycle-induced symptom is expected to occur.

10. The method of claim 1, wherein said administering occurs during the time at which said menstrual-cycle-induced symptom is expected to occur, or has occurred.

11. The method of claim 1, wherein said administering is discontinued at the time at which said menstrual-cycle-induced symptom is relieved.

12. The method of claim 1, wherein said administering is discontinued 1-7 days from onset of menses.

13. The method of claim 1, wherein said administering is discontinued 2-5 days from onset of menses.

14. The method of claim 1, wherein said administering is discontinued 1-7 days from conclusion of menstruation.

15. The method of claim 14, wherein said administering is discontinued 2-5 days from conclusion of menstruation.

16. The method of claim 1, wherein said at least one menstrual-cycle-induced symptom is a somatic symptom.

17. The method of claim 1, wherein said at least one menstrual-cycle-induced symptom is a mood and/or behavioral symptom.

18. The method of claim 17, wherein said at least one menstrual-cycle-induced symptom is selected from the group consisting of lethargy, eating disorders, forgetfulness, sleep disturbances, appetite changes, poor concentration, decreased interest, social withdrawal, irritability, mood swings, anxiety, tension, depression and feelings of lack of control.

19. The method of claim 1, wherein said at least one menstrual-cycle-induced symptom comprises at least two or more symptoms.

20. The method of claim 1, wherein said 3-MMC is administered in an amount in the range of 5 to 100 mg per administration.

21. The method of claim 1, wherein said 3-MMC is administered in an amount in the range of 10-65 mg per administration.

22. The method of claim 1, wherein said 3-MMC is administered in an amount of 12.5, 25, 35, 40 or 50 mg per administration.

23. The method of claim 1, wherein said 3-MMC is administered in an amount of 25 mg per administration.

* * * * *

UNITED STATES PATENT AND TRADEMARK OFFICE
CERTIFICATE OF CORRECTION

| | | |
|---|---|---|
| PATENT NO. | : 11,559,502 B2 | |
| APPLICATION NO. | : 17/637859 | |
| DATED | : January 24, 2023 | |
| INVENTOR(S) | : Merel Janssen et al. | |

It is certified that error appears in the above-identified patent and that said Letters Patent is hereby corrected as shown below:

On the Title Page

In item (72) Inventors, Line 2:
"Jochem Stijn Edgar"
Should be changed to:
--Jochem Stijn Edgar Janssen--

Signed and Sealed this
Twenty-fifth Day of July, 2023

Katherine Kelly Vidal
*Director of the United States Patent and Trademark Office*